(12) United States Patent
Barrai et al.

(10) Patent No.: US 10,669,488 B2
(45) Date of Patent: Jun. 2, 2020

(54) HYDROCARBON PYROLYSIS

(71) Applicant: ExxonMobil Chemical Patents Inc., Baytown, TX (US)

(72) Inventors: Federico Barrai, Houston, TX (US); James R. Lattner, La Porte, TX (US); Frank Hershkowitz, Basking Ridge, NJ (US); Elizabeth G. Mahoney, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/320,396

(22) PCT Filed: Aug. 15, 2017

(86) PCT No.: PCT/US2017/046871
§ 371 (c)(1),
(2) Date: Jan. 24, 2019

(87) PCT Pub. No.: WO2018/044547
PCT Pub. Date: Mar. 8, 2018

(65) Prior Publication Data
US 2019/0276748 A1    Sep. 12, 2019

Related U.S. Application Data

(60) Provisional application No. 62/381,722, filed on Aug. 31, 2016.

(51) Int. Cl.
| | | |
|---|---|---|
| *C10G 9/26* | (2006.01) | |
| *B01J 6/00* | (2006.01) | |
| *C10G 9/00* | (2006.01) | |

(52) U.S. Cl.
CPC ................ *C10G 9/26* (2013.01); *B01J 6/008* (2013.01); *C10G 9/002* (2013.01); *C10G 2400/20* (2013.01)

(58) Field of Classification Search
CPC .. C07C 5/32; C07C 11/04; C07C 4/04; C07C 5/327; C07C 11/24; C10G 9/26; B01J 19/2415; B01J 8/0438; B01J 19/24; B01J 8/0496; B01J 19/24858; B01J 19/04; B01J 2208/00513; B01J 2219/0076; B01J 2208/00548; B01J 2019/00087; B01J 2219/00164; B01J 2219/14
See application file for complete search history.

(56) References Cited

U.S. PATENT DOCUMENTS

| | | |
|---|---|---|
| 7,846,401 B2 | 12/2010 | Hershkowitz et al. |
| 2009/0250377 A1 | 10/2009 | Chun et al. |
| 2010/0290978 A1 | 11/2010 | Chun et al. |
| 2016/0176781 A1 | 6/2016 | Hershkowitz et al. |

*Primary Examiner* — Jafar F Parsa

(57) ABSTRACT

The invention relates to hydrocarbon pyrolysis, to equipment and materials useful for hydrocarbon pyrolysis, to processes for carrying out hydrocarbon pyrolysis, and to the use of hydrocarbon pyrolysis for, e.g., hydrocarbon upgrading.

23 Claims, 6 Drawing Sheets

HYDROCARBON PYROLYSIS

CROSS-REFERENCE TO RELATED APPLICATIONS

This application is a National Stage Application of International Application No. PCT/US2017/046871 filed Aug. 15, 2017, which claims the benefit of U.S. Patent Application Ser. No. 62/381,722, filed Aug. 31, 2016, which is incorporated herein by reference. Cross reference is made to the following related patent applications: U.S. Patent Application Ser. No. 62/402,009, filed Sep. 30, 2016, U.S. Patent Application Ser. No. 62/466,050, filed Mar. 2, 2017, U.S. Patent Application Ser. No. 62/486,545, filed Apr. 18, 2017, and PCT Patent Application No. PCT/US2017/046879, filed Aug. 15, 2017, which are incorporated by reference herein.

FIELD

The invention relates to hydrocarbon pyrolysis, to equipment and materials useful for hydrocarbon pyrolysis, to processes for carrying out hydrocarbon pyrolysis, and to the use of hydrocarbon pyrolysis, e.g., for upgrading gaseous and liquid hydrocarbon.

BACKGROUND

Olefinic compounds are a class of hydrocarbon compounds which have at least one double bond of four shared electrons between two carbon atoms. In part as a result of their utility as feeds for producing desirable products, olefin demand continues to grow, particularly for light olefin such as ethylene, propylene, and butenes.

Steam cracking is a commercially-available technology for producing light olefin from hydrocarbon-containing feeds. Although ethylene is the primary light olefin product of steam cracking, the process can also produce appreciable yields of propylene and butenes. Since steam cracking process conditions are selected to provide a fixed, predetermined feed conversion, ethylene, propylene and butylene yields are substantially constant.

During steam cracking, the feed is pyrolysed in the presence of added steam, which lessens coke yield, e.g., by decreasing hydrocarbon partial pressure. Even with added steam, however, the pyrolysis produces an appreciable yield of coke and coke precursors, and a portion of the coke accumulates in steam cracker furnace tubes.

Accumulating coke leads to both an undesirable pressure-drop increase across the tubes' internal flow path and a decrease in heat transfer to the feed-steam mixture. To overcome these difficulties, at least a portion of accumulated coke is removed from the interior of a tube by switching the tube from pyrolysis mode to decoking mode. During decoking mode, the flow of feed-steam mixture into the tube is terminated, and a flow of decoking fluid is established instead. The decoking fluid, typically comprising air and/or steam, reacts with and removes the accumulated coke. When sufficient coke has been removed, the tube is switched from decoking mode to pyrolysis mode to resume light olefin production. Although periodic decoking mode operation is effective for lessening the amount of accumulated coke, this benefit is obtained at a substantial energy cost. In part to lessen damage to the furnace tubes. e.g., by repeated thermal expansion/contractions, the fired heaters operate not only during pyrolysis mode, but also during decoking mode, even though an appreciable amount of recoverable light olefin is not produced during decoking mode.

In order to increase energy efficiency and improve the yield of light unsaturated hydrocarbon, processes have been developed which carry out the pyrolysis in a regenerative pyrolysis reactor. Such reactors generally include a regenerative thermal mass having at least one internal channel. The thermal mass is preheated, and then a flow of the hydrocarbon-containing feed is established through the channel. Heat is transferred from the thermal mass to the hydrocarbon feed, which increases the hydrocarbon feed's temperature and results in conversion of at least a portion of the feed by pyrolysis. The pyrolysis produces a pyrolysis product comprising molecular hydrogen, methane, acetylene, ethylene, and $C_{3+}$ hydrocarbon. The $C_{3+}$ hydrocarbon includes coke and coke precursors. Some coke remains in the passages of the thermal mass, and the remainder of the pyrolysis product is conducted away from the reactor as a pyrolysis effluent. Since the pyrolysis is endothermic, pyrolysis mode operation will eventually cool the thermal mass. e.g., to a temperature at which the pyrolysis reactions diminish or terminate. Pyrolysis conditions can be restored by regenerating the thermal mass during a heating mode. During heating mode, the flow of hydrocarbon-containing feed to the regenerative pyrolysis reactor is terminated. Flows of oxidant and fuel are established to the reactor, typically in an average flow direction that is substantially the reverse of the feed flow direction. Combustion of the fuel and oxidant reheats the thermal mass to a temperature sufficient for carrying out pyrolysis. The reactor can then be switched from heating mode to pyrolysis mode.

U.S. Patent Application Publication No. 2016-176781 discloses operating the pyrolysis mode in an elongated tubular reactor The reference (e.g., in its FIG. 1A) discloses controlling the pyrolysis mode for increased ethylene selectivity and decreased selectivity for coke and methane by establishing a sharp thermal gradient in the bulk gas temperature profile between a region of substantially constant temperature at which the pyrolysis can occur and a substantially constant lower temperature at which pyrolysis does not occur. During pyrolysis, the position of the gradient within the tubular reactor moves inward as the reactor cools, i.e., toward the midpoint of the reactor's long axis. The cooled reactor is then switched to heating mode, during which the gradient moves outward, i.e., away from the midpoint of the reactor's long axis. Although utilizing such pyrolysis conditions results in a coke yield that is less than that of steam cracking, some coke does accumulate in the channel. Advantageously, the reference reports that accumulated coke can be oxidized to volatile products such as carbon dioxide during heating mode by combustion using a portion of the oxidant in the oxidant flow. Energy efficiency is increased over steam cracking because (i) heating is not needed during pyrolysis mode and (ii) heat released by coke combustion in passages of the thermal mass during heating mode aids thermal mass regeneration. Although the process is more energy efficient than steam cracking, the process exhibits significant variations in coke and acetylene yields during pyrolysis mode, leading to difficulties in product separations downstream of the pyrolysis.

Energy efficient pyrolysis processes are now desired which have flexibility to produce a range of light olefin products, but with less variation in coke and acetylene yields.

SUMMARY OF THE INVENTION

The invention is based in part on the discovery that, contrary to the teachings of the prior art, it is beneficial to establish a bulk gas temperature profile during the pyrolysis that does not exhibit a sharp gradient between a substantially constant higher temperature region and a substantially constant lower temperature region. It has been found to be beneficial for certain features of the bulk gas temperature profile to exhibit a temperature decrease of ≤100° C. during the course of the pyrolysis. Doing so results moderates coke and acetylene yields during the pyrolysis, leading to a significant simplification of olefin recovery and purification systems.

Accordingly, certain aspects of the invention relate to pyrolysing a feed comprising ≥1 wt. % of $C_{2+}$ hydrocarbon, wherein the feed has a pyrolysis heat of reaction ($\Delta H$ in cal./mol). The pyrolysis is carried out in at least one elongated flow-through reactor having (i) an internal volume which includes first and second regions, opposed first and second openings in fluidic communication with the internal volume, wherein the first and second openings are separated by a reactor length ($L_R$), and (ii) a first channeled thermal mass located in the first region. The first channeled thermal mass has a solid density ($\rho_s$) ≤12 g/cm³, a heat capacity ($C_P$) ≤0.5 cal/g° C., and an open frontal area (OFA) ≤55%. The first channeled thermal mass includes a first aperture, the first aperture being proximate to the first opening and in fluidic communication with the first opening, and at least one internal channel in fluidic communication with the first aperture. The first channeled thermal mass also includes a second aperture, the second aperture being in fluidic communication with the first aperture via a flowpath $L_1$ through the channel. $L_1$ being ≥0.1*$L_R$. The process is carried out under preselected conditions for pyrolysing the feed in the internal channel, wherein the pyrolysis conditions include a residence time in the channel $t_R$ ≤0.1 sec., an average feed conversion (X) ≥50%, an average total pressure in the channel (P) ≥1 bar, an average bulk gas temperature in the channel ($T_{av}$) ≤1500° C. at the start of the pyrolysis, a change in average bulk gas temperature during the pyrolysis ($\Delta T_{av}$) ≤100° C. A reference pyrolysis step time ($t_{ref}$) is determined from the formula:

$$t_{ref}=(t_R*\rho_s*C_p*R*T_{av}*\Delta T_{av})*([1-OFA]*OFA_{-1})* (X*\Delta H*P)^{-1},$$

where R is substantially equal to the feed's Gas Constant. The process further includes establishing a flow of the feed into the channel toward the second aperture at a flow rate ≥0.01 kg/s by introducing the feed through the first opening and through the first aperture. The feed flow's $C_{2+}$ hydrocarbon is pyrolysed in the channel under the preselected pyrolysis conditions during a pyrolysis time interval $t_P$ which cools the first channeled thermal mass and produces a flow of a pyrolysis product. When $t_{ref}$ is >0.001 second, $t_P$ is ≤$t_{ref}$. When $t_{ref}$ is ≤0.001 second, $t_P$ is 0.001 second. The pyrolysis product comprises molecular hydrogen, acetylene. $C_{2+}$ olefin, and coke. During $t_P$, the flow of at least a portion of the pyrolysis product is conducted into the second region of the internal volume via the second aperture, and away from the reactor via the second opening.

Other aspects of the invention also relate to pyrolysis of such a feed in such a pyrolysis reactor. These aspects differ from the previous aspects in that the range of pyrolysis time interval $t_P$ is fixed in a range of from 0.001 sec. to 50 sec., and the OFA of the first thermal mass is determined from the relationship:

$$([OFA-1]/OFA)=(t_R*\rho_s*C_p*R*T_{av}*\Delta T_{av})^{-1}* (t_P*X*\Delta H*P).$$

As in the preceding aspects, the process further includes establishing a flow of the feed into the channel toward the second aperture at a flow rate ≥0.01 kg/s by introducing the feed through the first opening and through the first aperture. The feed flow's $C_{2+}$ hydrocarbon is pyrolysed in the channel under the preselected pyrolysis conditions during a pyrolysis time interval $t_P$ which cools the first channeled thermal mass and produces a flow of a pyrolysis product comprising molecular hydrogen, acetylene, $C_{2+}$ olefin, and coke. During $t_P$, the flow of at least a portion of the pyrolysis product is conducted into the second region of the internal volume via the second aperture, and away from the reactor via the second opening.

In still other aspects, the invention relates to a regenerative pyrolysis reactor for carrying out any of the preceding aspects, and to the resulting pyrolysis products.

DETAILED DESCRIPTION

Definitions

Figure 1:
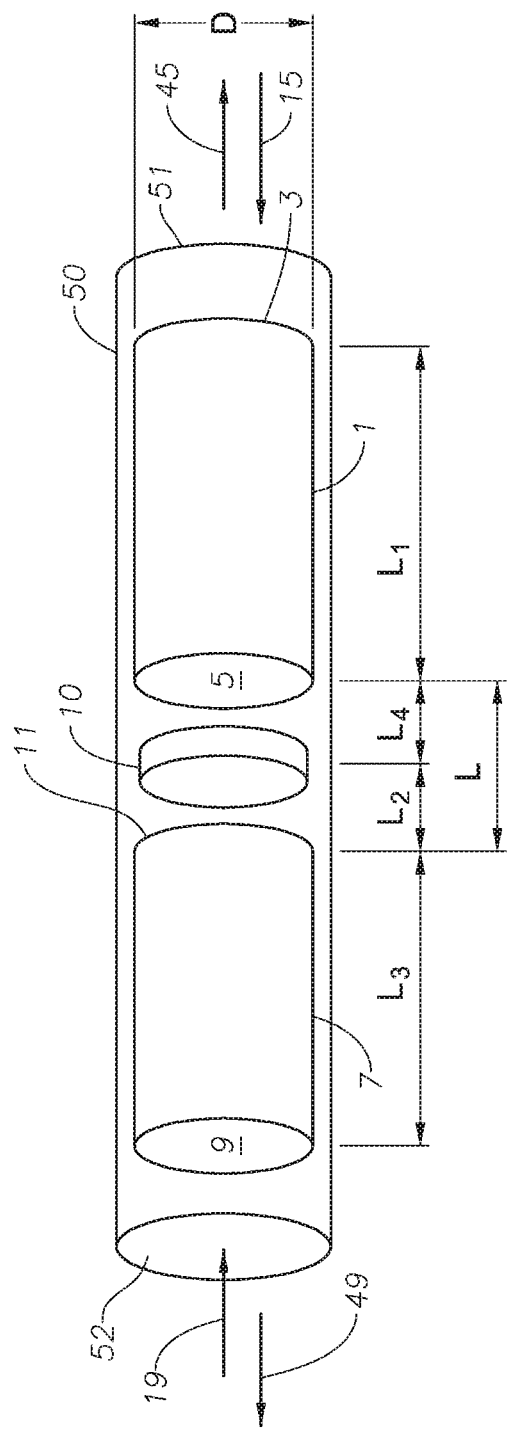
FIG. 1 schematically shows one form of a reverse flow reactor that is suitable for carrying out certain aspects of the invention.

For the purpose of this description and appended claims, the following terms are defined.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only. e.g., those containing ≤1% (molar basis) of unsaturated carbon atoms. The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring.

The terms "reactor", "reactor system". "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. A "pyrolysis reactor" is a reactor, or combination of reactors or a system for hydrocarbon pyrolysis. The term "pyrolysis stage" means at least one pyrolysis reactor, and optionally including means for conducting one or more feeds thereto and/or one or more products away therefrom. A "region" or "zone" is a location, e.g., a specific volume, within a reactor, a location between two reactors and/or the combination of different disjointed locations in one or more reactors. A "pyrolysis region" is a location where pyrolysis is carried out, e.g., in a location which contains or is proximate to components, such as at least one thermal mass, which provides heat for the pyrolysis. A reactor or reaction stage can encompass one or more reaction regions. More than one reaction can be carried out in a reactor, stage, or region.

A pyrolysis region can include components, e.g., one or more thermal masses, having conduits, channels, and passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, with the channel having a plurality of passages or sets of passages.

A channeled thermal mass is a reactor component (e.g., a flow-control component) comprising refractory material such as one or more of alumina, silica, zirconia, yttria, etc. The refractory has a mass density $\rho_s$, referred to herein as a "solid density", and a heat capacity $C_P$ (measured at 25° C.) that is typically ≥0.05 cal./g° C. The channeled thermal mass has an open frontal area ("OFA") for passing fluid into the channel(s), where OFA has the same meaning as in U.S. Pat. No. 5,494,881, which is incorporated by reference herein in its entirety.

The term "bulk gas temperature" means the temperature of a bulk gas steam as measured by a device (such as a thermocouple) that is in contact with the bulk gas but not in contact with a solid thermal mass. For example, if the gas is traveling through an internal channel of length L of a thermal mass in the pyrolysis zone of a thermal pyrolysis reactor, the bulk gas temperature at a location along $L_c$ is the average temperature (arithmetic mean) over the channel's cross sectional area at that location. The peak gas temperature ("$T_P$") is the greatest cross-sectional-averaged bulk gas temperature achieved along a flowpath, e.g., within a passage of a channel. When the thermal profile over the length of a flow path exhibits more than one local maximum, $T_P$ corresponds to the local maximum having the greatest bulk gas temperature. One skilled in the art will appreciate that a gas temperature immediately proximate to a solid thermal mass, such as a partition between passages within a thermal mass at any particular location may exceed the bulk gas temperature, and may, in some infinitesimal layer, actually approach the solid's temperature. The average bulk gas temperature "$T_{av}$" over a region of the reactor, e.g., the pyrolysis zone or, a flow path, a channel, a passage, etc. $T_{av}$ at a particular time (e.g., at the start of pyrolysis) is obtained using the formula:

$$Tav = \left[ \frac{1}{b-a} \int_a^b T(x)dx \right]$$

Figure 2:
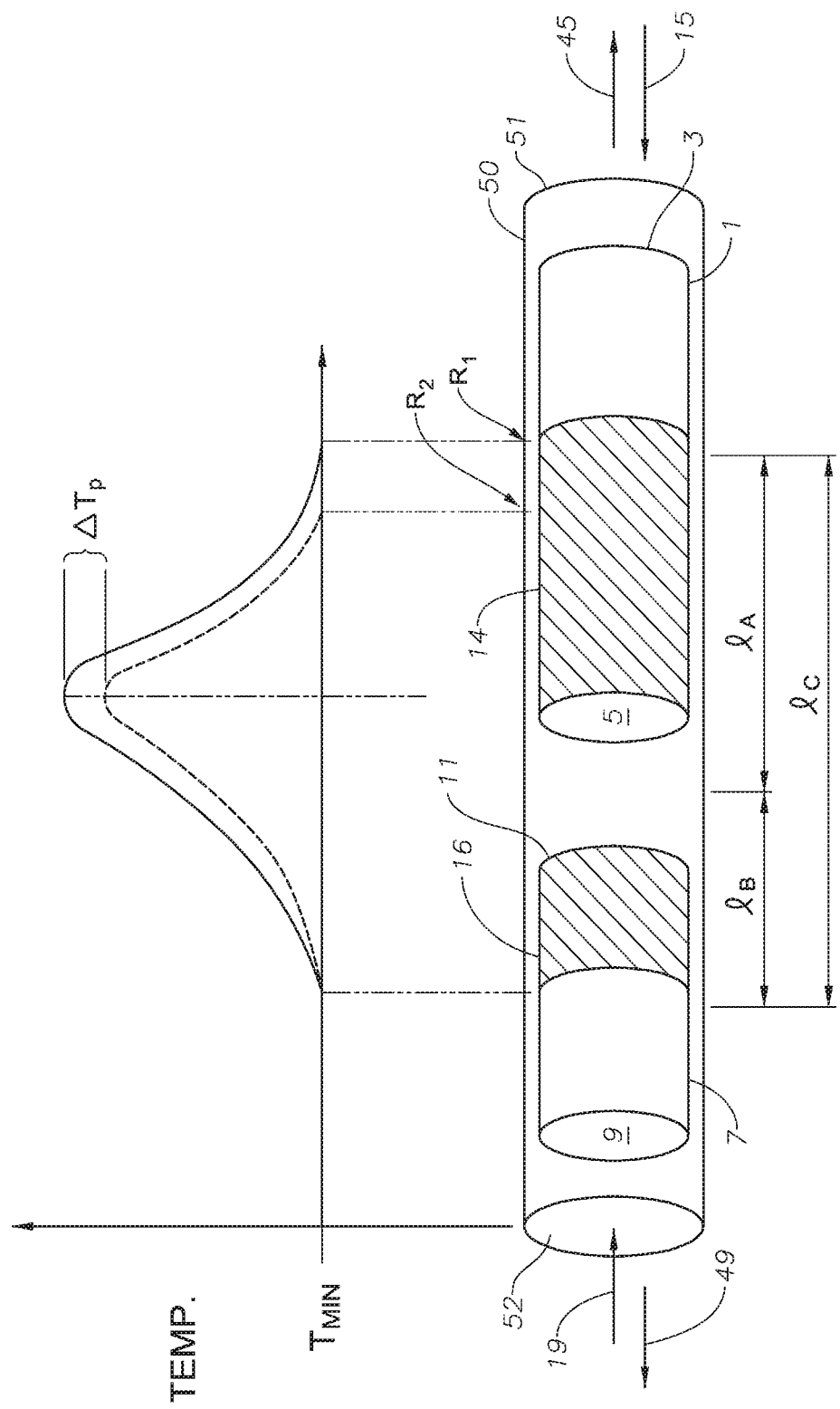
FIGS. 2 and 3 schematically show forms of a reverse flow reactor and representative bulk gas temperature profiles at the start (solid lines) and end (dashed lines) of pyrolysis mode.
Figure 3:
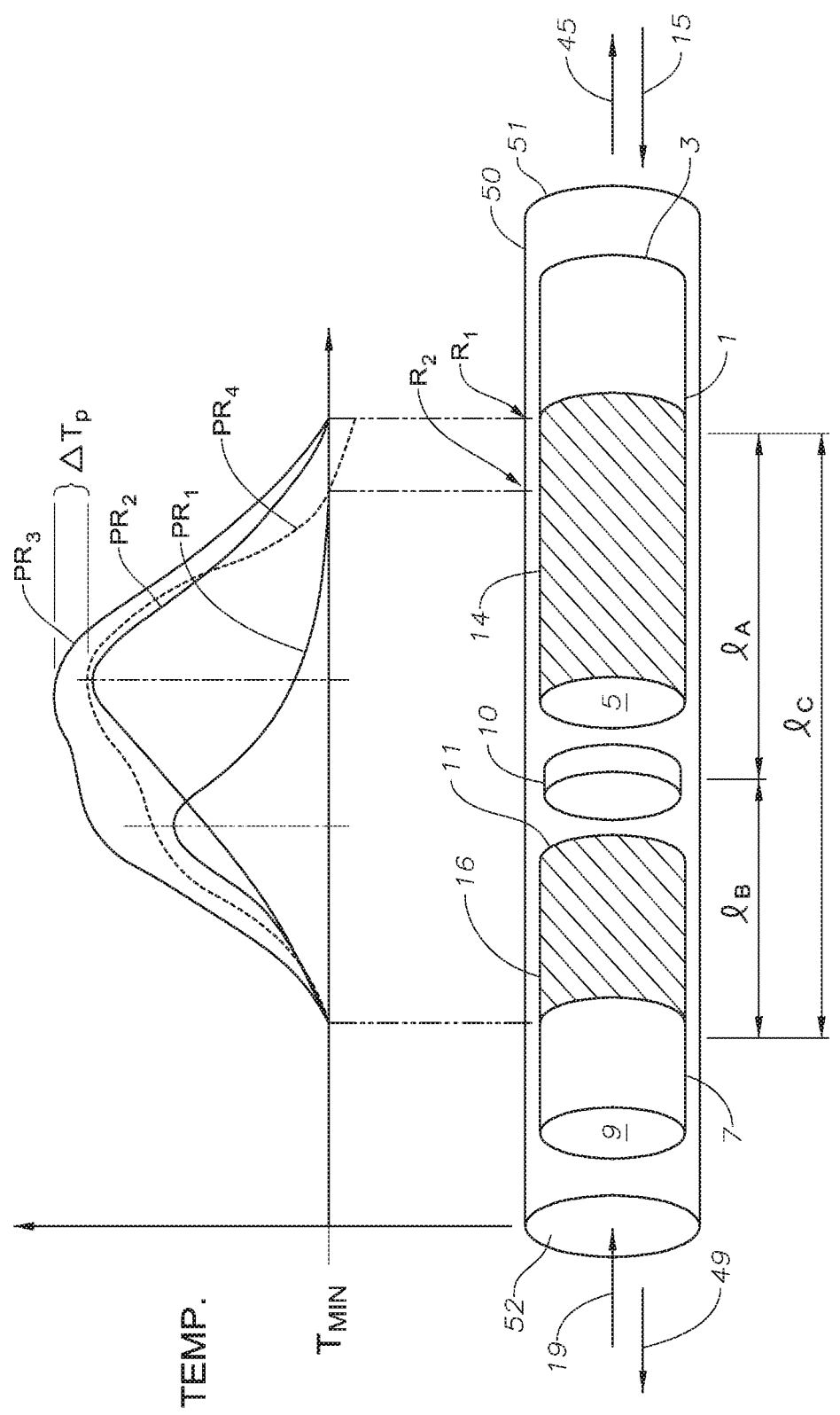

Parameters a and b are the boundaries of an interval (distance) along the long axis of the reactor. For example, referring to FIG. 1, parameter "a" can be the position of aperture 50 and parameter "b" can be the position of aperture 9. T(x) is a function representing the variation of bulk gas temperature over the interval of from a to b. When T(x) is a bulk gas temperature profile of a pyrolysis zone, e.g., the pyrolysis zones indicated (at the start of $t_P$) by the shaded regions in FIGS. 2 and 3, parameters a and b are the locations where the bulk gas temperature profile intersects the line $T_{MIN}$, which corresponds to the minimum temperature at which feed conversion is ≥10% under the selected pyrolysis conditions and feed. Since the bulk gas temperature profile typically changes during the pyrolysis time interval $t_P$, as shown in FIGS. 2 and 3, $T_{av}$ will typically decrease during $t_P$. The portion of the profile having a temperature ≥$T_{MIN}$ can be continuous, but this is not required. For example, when a profile that intersects $T_{MIN}$ at more than two locations in the pyrolysis zone (e.g., a, b) and touches $T_{MIN}$, at a location c (not shown, but between a and b), additional integrations are carried out, e.g.:

$$Tav = \frac{1}{b-a} \int_a^b T(x)dx + \frac{1}{c-b} \int_b^c T(x)dx.$$

When the portion of the profile that is ≥$T_{MIN}$ is in the form of discrete segments, the integrations are performed over each of the segments.

The term "selectivity" refers to the production (weight basis) of a specified compound in a reaction. As an example, the phrase "a hydrocarbon pyrolysis reaction has 100% selectivity for methane" means that 100% of the hydrocarbon (weight basis) that is converted in the pyrolysis reaction is converted to methane. When used in connection with a specified reactant, the term "conversion" means the amount of the reactant (weight basis) consumed in the reaction. For example, when the specified reactant is ethane, 100% conversion means 100% of ethane is consumed in the reaction. With respect to hydrocarbon pyrolysis the term "conversion" encompasses any molecular decomposition by at least pyrolysis heat, including cracking, breaking apart, and reformation. Average conversion ("X") in a reaction zone, e.g., a pyrolysis zone, is the conversion achieved at $T_{av}$. Yield (weight basis) is conversion time selectivity.

The term "pyrolysis" means an endothermic reaction for converting molecules into (i) atoms and/or (ii) molecules of lesser molecular weight, and optionally (iii) molecules of greater molecular weight, e.g., processes for converting ethane and/or propane to molecular hydrogen and unsaturates such as ethylene, propylene and acetylene. Certain aspects of the invention feature a pyrolysis zone exhibiting selectivities (e.g., of desired products) which vary as a function of position along the length of the pyrolysis zone but which do not vary appreciably as a function of time during pyrolysis mode, e.g., within about +/−25%, such as +/−10%, or +/−5% from selectivity at the start of $t_P$. More particularly, for certain aspects in which $T_{av}$ and/or $T_P$ decrease by ≤100° C. during pyrolysis mode, the yield of many desired products, e.g., light olefin yield, such as ethylene and/or propylene yield, do not vary appreciably as a function of time during pyrolysis mode even though the product selectivities vary as a function of position along the length of the pyrolysis zone. For example, yield is typically within about +/−25%, such as +/−10%, or +/−5% of yield at the start of $t_P$. In these aspects, average conversion might not vary appreciably as a function of time during pyrolysis mode, typically within about +/−25%, such as +/−10%, or +/−5% of average conversion at the start of $t_P$.

A hydrocarbon feed is subjected to "thermal pyrolysis" when <50.0% of the heat utilized by the pyrolysis is provided by exothermically reacting the hydrocarbon feed, e.g., with an oxidant. The invention encompasses forms of thermal pyrolysis wherein ≤40.0% of the heat utilized by the pyrolysis is provided by exothermically reacting the hydrocarbon feed, e.g., ≤25.0%, such as ≤10.0%. In certain aspects substantially no heat for the pyrolysis is provided by exothermically reacting the hydrocarbon feed. The "severity threshold temperature" for pyrolysis is the lowest bulk gas temperature at which acetylene selectivity is at least 10% for a total residence time ≤0.1 second. High-severity pyrolysis conditions are those carried out at a peak gas temperature that is greater than or equal to the severity threshold temperature. Low-severity pyrolysis conditions are those carried out at a peak gas temperature that is less than the severity threshold temperature, i.e. conditions under which substantially no hydrocarbon pyrolysis is carried out at a pyrolysis gas temperature that exceeds the severity threshold temperature. High-severity conditions include those which exhibit (i) a methane selectivity ≥5 wt. % and/or (ii) a propylene selectivity at a temperature ≥1000° C. of ≤0.6 wt. %. With respect to pyrolysis reactors, the term "total residence time" means the average time duration for substantially non-reacting (non-converting by pyrolysis) molecules (such as He, $N_2$, Ar) having a molecular weight in the range of 4 to 40 to traverse a pyrolysis region of a pyrolysis reactor. The term "gas residence time" means the residence time average time of a substantially non-liquid molecules.

The term "Periodic Table" means the Periodic Chart of the Elements, as it appears on the inside cover of The Merck Index, Twelfth Edition, Merck & Co., Inc., 1996.

Certain aspects of the invention relate to carrying out pyrolysis mode and heating mode under the specified conditions in one or more reverse flow reactors. Representative reverse flow reactors will now be described in more detail with respect to FIG. 1. The invention is not limited to these aspects, and this description is not meant to foreclose the use of other reactors within the broader scope of the invention.
Representative Reverse Flow Reactors Reactor 50 is a reverse-flow reactor having the form of an elongated tubular vessel having an internal volume which includes a pyrolysis zone for carrying out the pyrolysis. Typically, the internal volume includes three zones: a first heat-transfer zone, a second heat transfer zone, with the pyrolysis zone being located between the first and second heat transfer zones. The zones are in fluidic communication with one another. The reactor vessel's cross sectional shape and/or cross sectional area can be substantially uniform over the length of the reactor, but this is not required. For example, one or more segments of the reactor vessel's length can have a circular, elliptical, or polygonal cross section. Reactor 50 has opposed first and second openings 51 and 52 which are in fluidic communication with the internal volume and are located at terminal ends of the reactor vessel.

Reactor 50 includes first and second thermal masses 1 and 7 for transferring heat to/from reactants and products during the pyrolysis and heating modes. The thermal masses are channel members comprising refractory. Typically, the thermal masses comprise bedding or packing material that is effective in storing and transferring heat, such as glass or ceramic beads or spheres, metal beads or spheres, ceramic (e.g., ceramics, which may include alumina, yttria, and zirconia) or honeycomb materials comprising ceramic and/or metal, other forms of tubes comprising ceramic and/or metal, extruded monoliths and the like. The thermal masses and regenerative beds containing thermal masses can be in the form of a refractory channeled member, e.g., those described in U.S. Pat. Nos. 8,754,276; 9,126,882; 9,346,728; 9,187,382; 7,943,808; 7,846,401; 7,815,873; 9,322,549; and in U.S. Patent Application Publications Nos. 2007-0144940, 2008-300438, 2014-303339, 2014-163287, 2014-163273, 2014-0303416, 2015-166430, 2015-197696, and 2016-176781. These references are incorporated by reference herein in their entireties.

Certain aspects of the invention relate to limiting decreases in $T_p$ and/or $T_{av}$ during pyrolysis mode (e.g., during $t_P$) to about 100° C. or less, e.g., ≤75° C. such as ≤50° C., or ≤25° C., or ≤10° C., or ≤5° C. Since the temperature profile during pyrolysis varies over the length of the pyrolysis zone, and typically over the entire length of the reactor, $T_P$ is $>T_{av}$. It has been found that this can be accomplished for a wide range of pyrolysis conditions by carrying out the pyrolysis in a regenerative pyrolysis rector which includes a thermal mass having at least one channel, wherein the thermal mass has a solid density ($\rho_s$) ≤12 g/cm³, a heat capacity ($C_P$) ≤0.5 cal/g° C. and an OFA that is obtained from predetermined pyrolysis conditions using the equation:

$$([OFA-1]/OFA) = (t_R * p * C_p * R * T_{av} * \Delta T_{av})^{-1} * (t_P * X * \Delta H * P). \tag{I}$$

In evaluating equation I, ΔH is the pyrolysis feed's heat of reaction under the pyrolysis conditions, e.g., ≥20,000 cal./mol.; $t_R$ is the residence time in the channel during the pyrolysis, e.g., $t_R$ ≥1 Sec.; X is the conversion of the feed to the pyrolysis reactor, e.g., X≥50%; P is the average total pressure in the channel during the pyrolysis, e.g., P ≥1 bar; $T_{av}$ is the average bulk gas temperature in the channel at the start of the pyrolysis, e.g., $T_{av}$≤1500° C. at the start of pyrolysis; $\Delta T_{av}$ is the change in average bulk gas temperature in the pyrolysis zone during the pyrolysis; $t_P$ is the duration of pyrolysis mode operation in the reactor (the pyrolysis step time), e.g., $t_P$ in the range of from 0.001 sec. to 50 sec.; and R is substantially equal to the pyrolysis feed's Gas Constant, which can generally be approximated with sufficient accuracy under the specified pyrolysis conditions by the Ideal Gas Constant=83.1445 cm³ bar K⁻¹ mol⁻¹. Typically, the OFA of thermal mass 1 is in the range of about 10% to 55%, e.g., 10% to 50%, such as 10% to 45%, or 10% to 35%. For example, OFA can be ≤50%, such as ≤45%, or in the range of from 15% to 50%, or 15% to 45%, or 15% to 35%, or 20% to 50%, or 20% to 45%, or 20% to 35%.

The thermal mass typically has a thermal conductivity in the range of from 0.5 W/m° K to 50 W/m° K, a coefficient of thermal expansion in the range of from 1×10⁷/° K to 2×10⁻⁵/° K, and an average wetted surface area per unit volume in the range of from 1 cm⁻¹ to 100 cm⁻¹. The internal channel of the first thermal mass typically includes a plurality of substantially parallel passages, e.g., at a passage density in the range of from 77000/m² to 1.3×10⁶/m². The thermal mass comprises refractory, and the refractory generally has a specific heat capacity at (measured at 25° C.) that ≥0.05 cal./g ° C. (≥0.21 [kj/(° K kg)] and a $\rho_s$ ≤15 g/cm³. For example, the refractory's $C_P$ can be in the range of from 0.21 [kj/(K kg)] to 2.1 [kj/(K kg)], and its $\rho_s$ can be ≤8 g/cm$^3$, such as ≤5 g/cm$^3$, or in the range of from 2 g/cm$^3$ to 5 g/cm$^3$.

The choice of refractory composition is not critical, provided it is capable of surviving under pyrolysis mode and heating mode conditions for practical run lengths (e.g., months) without significant deterioration or decomposition. Those skilled in the art will appreciate that the compositions of the first and second thermal masses should be selected from among those that substantially maintain integrity (structural and compositions) and functionality during long term exposure to pyrolysis feeds, products, and reaction conditions, e.g., temperatures ≥750° C., such as ≥1200° C., or for increased operating margin ≥1500° C. Conventional refractories can be used, including those comprising at least one oxide of one or more elements selected from Groups 2-14 of the Periodic Table, but the invention is not limited thereto. In particular aspects, the refractory includes oxide of at least one of Al., Si, Mg, Ca, Fe, Mn, Ni, Co, Cr, Ti, Hf, V. Nb, Ta, Mo, W, Sc, La, Yt, Zr, and Ce. Alternatively or in addition, the refractory can include non-oxide cermic.

Continuing with reference to FIG. 1, a first segment of the first thermal mass 1 is located in a first heat transfer zone, which preheats the hydrocarbon feed for the pyrolysis. A second segment of thermal mass 1 is located in the pyrolysis zone. Likewise, a first segment of the second thermal mass 7 is located in a second heat transfer zone, which cools the pyrolysis product. A second segment of thermal mass 7 is located in the pyrolysis zone. Typically, thermal masses 1 and 7 have the form of an elongated tubular member comprising refractory and having at least one internal channel and opposed apertures in fluidic communication with the internal channel(s). Thermal mass 1 has a length $L_1$ and typically $L_1$ is substantially the same as the length of the internal channel, $L_c$. Thermal mass 7 has a length $L_3$, and typically $L_3$ is substantially the same as the length of the internal channel, $L_c$. $L_1$ (and also typically $L_3$) is ≥0.1*$L_R$, where $L_R$ is the total length of reactor 50. For example, $L_1$ can be in the range of from 0.1*$L_R$ to 0.9*$L_R$, such as 0.1*$L_R$ to 0.4*$L_R$. Optionally, $L_3$ is substantially the same length as $L_1$. Optionally thermal masses 1 and 7 have substantially the same composition, substantially the same cross-sectional shape, substantially the same cross sectional area, and substantially the same OFA. As shown in FIG. 1, thermal mass 1 includes first and second apertures 3 and 5, and thermal mass 7 includes first and second apertures 9 and 11. Aperture 3 is adjacent to opening 51. Optionally, particularly in aspects (not shown) in which thermal mass 7 is omitted, aperture 5 can be adjacent to opening 52. Thermal masses 1 and 7 can each have the form of an elongated honeycomb comprising at least one channel, the channel having a plurality of passages. When a thermal mass is a segmented thermal mass, the honeycombs can be arranged adjacent to one another (e.g., end-to-end, in series). As may be appreciated, it is desirable, e.g., to lessen reactor pressure drop, to a align passages of a honeycomb's internal channel or channels with those of neighboring honeycombs to facilitate fluidic communication through the thermal mass. Optionally, the segments are of substantially the same composition, shape, cross sectional area, OFA, and have substantially the same total number of passages and the same number of passages per unit area.

The internal volume of reactor 50 also includes a combustion zone, e.g., between terminal segments of the first and second thermal masses. It is within the scope of the invention for the combustion zone to include all of the reactor's internal volume between apertures 5 and 11, e.g., the entire length L shown in FIG. 1, but this is not required. Typically, however, the combustion zone is centered in the region between apertures 11 and 5, e.g., with $L_2$ being substantially equal to $L_4$. As may be appreciated, the combustion zone occupies a region of reactor 50's internal volume during $t_H$ that is within the pyrolysis zone during $t_P$. However, since in the aspects illustrated in FIG. 1, a heating mode is not carried out at the same time as pyrolysis mode, appreciable combustion does not occur in the combustion zone during pyrolysis and appreciable pyrolysis does not occur in the pyrolysis zone during heating.

The combustion zone is typically configured for (i) mixing the fuel and a portion of the oxidant during heating mode for efficient combustion, (ii) increasing distribution uniformity over third zone's internal cross sectional area of the combustion products, unreacted oxidant, and optionally unreacted fuel, and (iii) lessening undesirable pressure-drop effects during pyrolysis mode. The combustion zone can have the form of an open volume within the internal volume of reactor 50. e.g., an open volume having a length L and substantially constant circular cross section of diameter D and cross sectional area A (not shown). As may be appreciated, an open volume having an appropriate L:A ratio will provide at least some mixing and distribution during heating mode without creating too great a pressure drop during pyrolysis mode. More typically, since it provides improved mixing and distribution and allows a lesser overall length for the combustion zone, the combustion zone includes at least one mixer-distributor apparatus 10. The mixer-distributor, which can have the form of a relatively thin member (e.g., a plate) having one or more orifices effective for carrying out the mixing and distribution during heating mode. Conventional mixer-distributors can be used, such as those described in U.S. Patent Application Publication No. 2013-0157205 A1 and U.S. Pat. No. 7,815,873 (incorporated by reference herein in their entireties), but the invention is not limited thereto. Optionally, the combustion zone contains at least one selective combustion catalyst. Suitable selective combustion catalysts are described in U.S. Pat. No. 8,754, 276, but the invention is not limited thereto. When used, a fixed bed of the selective combustion catalyst can be included as a component of mixer-distributor 10, e.g., with one or more of the mixer-distributor's plate members serving as a catalyst support. When used, mixer-distributor 10 can be located at any location within the combustion zone. Typically, however, it is located approximately mid-way between apertures 11 and 5, as shown. In certain aspects, however, such as those where the amount of coke deposits in thermal mass 1 exceed that of thermal mass 7, the combustion zone is shifted downstream (with respect to fuel-oxidant flow) toward thermal mass 1. The amount of shift is typically ≤25% of L, e.g., ≤20%, such as ≤10%.

The sum of lengths $L_1$, L, and $L_3$ is typically ≥90% of the total length of reactor 50 ($L_R$), e.g., as measured between openings 51 and 52. Since it is desirable to direct fuel and oxidant flows into appropriate passages of thermal mass 7 during heating mode and to direct pyrolysis feed flow into appropriate passages of thermal mass 1 during pyrolysis mode, it is typically desired to limit the internal volume between aperture 9 and opening 52 and between aperture 3 and opening 51, to that needed for convenient reactor assembly and to prevent component interference as might otherwise occur from thermal expansion during use. The pyrolysis zone, which generally encompasses all of region L, a segment of $L_1$, and a segment of $L_3$, is typically ≥10% of the total length of reactor 50, e.g., ≥15%, such as ≥20%. It is also typical for the pyrolysis zone to encompass ≤80% of $L_R$, e.g., to leave sufficient internal volume of thermal mass 1 for pre-heating the pyrolysis feed and sufficient internal volume of thermal mass 7 for quenching the pyrolysis product, e.g., ≤60%, such as ≤40%. In certain aspects, the pyrolysis zone has a length in the range of from 10% to 60% of $L_R$, e.g., in the range of from 20% to 40%. The combustion zone's length L is typically ≤50% of that of the length of the pyrolysis zone, e.g., ≤40%, such as ≤30%, or ≤20%.

Values for $L_R$, L, $L_1$, $L_2$, $L_3$, $L_4$, and D generally depend on the pyrolysis feed used and the rate at which it is conducted into the reactor, the fuel and oxidant compositions, and the rate at which these are conducted into the reactor, etc. Although larger and small reactors are within the scope of the invention, (i) D is typically ≥1 cm, e.g., in the range of from about 1 cm to 10 m, such as 0.1 m to 7.5 m, (ii) $L_R$ is typically ≥1 cm, e.g., in the range of from about 1 cm to 20 m, such as 0.1 m to 7.5 m, (iii) L is typically ≤25% of $L_R$, e.g., ≤10%, (iv) $L_1$ is typically ≥35% of $L_R$ e.g., ≥45%, (v) $L_3$ is typically ≥35% of $L_R$, e.g., ≥45%, $L_3$ being optionally of substantially the same size and shape as $L_1$, and (vi) $L_2$ is typically within about +/−25% of $L_4$, e.g., +/−10%, such as +/−5%.

In certain aspects (not shown) at least a portion of the fuel-oxidant combustion is carried out in a location other than within the internal volume of reactor 50. For example, fuel combustion can be carried out at a location external to reactor 50, with the combustion products, unreacted oxidant, and optionally unreacted fuel being conveyed to the vicinity of the pyrolysis zone for (i) heating the pyrolysis zone to provide a desired temperature profile for efficiently carrying out the pyrolysis and (ii) combusting catalyst coke deposits with at least a portion of the unreacted oxidant.

In aspects illustrated schematically in FIG. 1, reactor 50 is heated during heating mode by conveying a heating mixture 19 comprising fuel and oxidant through opening 52, through aperture 9 of thermal mass 7, and out of aperture 11 toward mixer-distributor 10. Typically, the fuel and oxidant are conveyed separately through different channels of thermal mass 7 from aperture 9 toward aperture 11, and are combined to form the heating mixture downstream (with respect to fuel/oxidant flow) of thermal mass 7. Typically fuel and oxidant are heated by a transfer of heat from thermal mass 7 as the fuel and oxidant flow through the channels of thermal mass 7. Combustion of the fuel and oxidant produces a combustion product. Combustion product, any un-combusted oxidant, and any un-combusted fuel enter aperture 5. When there is un-combusted oxidant in thermal mass 1, this can react with coke deposits and any un-combusted fuel to produce additional combustion product. An aggregated combustion product 45 is conducted out of aperture 3 and away from the reactor via opening 51. The aggregate combustion product typically comprises the combustion product produced in combustion zone 10; additional combustion product, typically from combustion of coke in passages of thermal mass 1; and any unreacted fuel and/or any unreacted oxidant. Reactor 50 is switched from heating mode to pyrolysis mode after achieving the desired reactor temperature profile.

Continuing with reference to FIG. 1, a pyrolysis feed 15 is conducted into reactor 50 during pyrolysis mode via opening 51. The pyrolysis feed is preheated in an upstream segment of thermal mass 1 and is typically pyrolysed in (i) a downstream segment of thermal mass 1, and optionally also in (ii) the region between thermal mass 1 and thermal mass 7 and (iii) in an upstream segment of thermal mass 7, upstream and downstream now being with respect to the flow of feed and pyrolysis product. A volatile portion 49 (typically gaseous) of the pyrolysis product is cooled in a downstream segment of thermal mass 7, and is conducted away from thermal mass 7 via aperture 9, and is conducted away from reactor 50 via opening 52. A non-volatile portion of the pyrolysis product remains in the reactor, typically as coke deposits. Accumulation of coke deposits in reactor 50 is lessened by combusting deposited coke during heating mode.

Heating mode is carried out for a time interval of duration $t_H$ to achieve a desired temperature profile in the internal volume of reactor 50 for the start of pyrolysis mode, primarily by fuel-oxidant combustion in the combustion zone, coke-oxidant combustion in passages of thermal masses 1 and 7, and optionally additional fuel-oxidant combustion in internal passages of thermal mass 1 and (less typically) thermal mass 7. Pyrolysis mode is carried out for a time interval of duration $t_P$. Pyrolysis is endothermic, and, consequently, the bulk gas temperature profile of reactor 50 is transformed over the course of time interval $t_P$ to a profile that is not appropriate for efficient pyrolysis. Reactor 50 is then switched from pyrolysis mode to heating mode to reheat the reactor, so that the desired bulk gas temperature profile is exhibited at the start of a following pyrolysis mode. Typically, at least one flow controller is provided to (i) establish forward flows of the pyrolysis feed and the pyrolysis product during pyrolysis mode for a time duration $t_P$ and (ii) establish reverse flows of the fuel, the oxidant, and the combustion product during heating mode for a time duration $t_H$.

Pyrolysis mode and heating mode are typically repeated in sequence, for semi-continuous or continuous operation. Intervening steps between successive pyrolysis and heating modes, e.g., one or more steps for admitting a forward or reverse flow of sweep gas to the reverse-flow reactor, can be carried out between pyrolysis mode and heating mode operation, and vice versa. Continuous or semi-continuous operation can be characterized by a "cycle time", which constitutes the time duration from the start of a pyrolysis mode to the start of the next pyrolysis mode in the sequence, and includes the time duration of heating mode(s) and any intervening steps (when used). Cycle time can be substantially constant over a plurality of repeated cycles, but this is not required. The invention is typically practiced with relatively short cycle times compared to that of conventional processes (e.g., steam cracking) for pyrolysing similar feed hydrocarbon at a peak pyrolysis temperature ≤1200° C. For example, cycle time can be ≤60 seconds, e.g., ≤30 seconds, such as ≤15 seconds, or ≤5 seconds. Typically, cycle time is in the range of from 2 seconds to 60 seconds, e.g., 3 second to 30 seconds, such as 4 second to 30 seconds. When (i) the pyrolysis feed is introduced into the reactor in a direction that is substantially opposite to the direction of fuel and oxidant flow and/or (ii) when the flow of pyrolysis product away from the reactor is substantially opposite to the direction of combustion product flow, the reactor is called a reverse-flow reactor.

Certain aspects of heating mode operation, during which reactor 50 is preheated for initial pyrolysis mode operation, or reheated for continued pyrolysis mode operation, will now be described in more detail. The invention is not limited to these aspects, and this description is not meant to foreclose other ways to operate a heating mode.

Representative Heating Mode Conditions

Operating conditions during heating mode are selected to accomplish (i) reheating the pyrolysis zone to establish a temperature profile in the reactor corresponding to the desired bulk gas temperature profile at the start of a following pyrolysis mode and (ii) removing sufficient coke deposits from within the reactor's internal volume, which would otherwise lead to an increase in reactor pressure drop. When it is desired to quench the pyrolysis product within the reactor, heating mode optionally includes cooling thermal mass within the reactor at a location that is both upstream (with respect to fuel-oxidant flow) of the combustion zone and downstream (with respect to the flow of pyrolysis product) of the pyrolysis zone.

Combustion is carried out during heating mode by reacting fuel and oxidant, e.g., fuel and oxidant contained in a heating mixture. The fuel and oxidant can be the same as those disclosed in U.S. Pat. No. 7,943,808. Optionally, the fuel is derived from, comprises, consists essentially of, or consists of one or more of hydrogen, CO, methane, methane containing streams, such as coal bed methane, biogas, associated gas, natural gas and mixtures or components thereof, etc. The fuel typically comprises one or more of molecular hydrogen, synthesis gas (mixtures of CO and $H_2$), and hydrocarbon, such as $\geq 10.0$ wt. % hydrocarbon, or $\geq 50.0$ wt. % hydrocarbon, or $\geq 90.0$ wt. % hydrocarbon. The oxidant is typically one or more of molecular oxygen, ozone, and air, including molecular oxygen in air. Those skilled in the art will appreciate that feed flow rate will depend on factors such as feed composition, reactor volume, pyrolysis conditions, etc. Accordingly, the invention can be carried out over a very wide range of heating mixture flow rates, e.g., at a flow rate $\geq 0.001$ kg/s, such as $\geq 0.1$ kg/s, or $\geq 10$ kg/s, or $\geq 100$ kg/s, or more.

Once a fuel of the desired caloric content (heating value) has been selected, the amounts of fuel and oxidant to the reactor during heating mode can be specified in terms of the amount of oxidant needed for combusting the accumulated coke deposits ("$OC_a$") and the amount of oxidant ("$OC_b$") needed for the substantially stoichiometric combustion of the fuel. Typically, the amount of oxidant supplied during heating mode is $Z \cdot (OC_a + OC_b)$, wherein Z is generally $\geq 0.5$, e.g., $\geq 0.8$, such as in the range of 0.5 to 5.0, or 0.5 to 3.0, or 0.8 to 3.0. The amounts $OC_a$ and $OC_b$ are on a molar basis. When $Z > 1.0$, the excess oxidant can be utilized, e.g., for one or more of removing at least a portion of any accumulated coke deposits, moderating the reaction temperature during heating mode (as disclosed in U.S. Pat. No. 7,943,808), and conveying heat within the reactor from one zone to another. Generally, a first portion of the oxidant is combusted with the fuel in the combustion zone, and a second portion is combusted with accumulated coke deposits. Typically, the first portion comprises $\geq 50$ wt. % of the total amount of oxidant supplied during heating mode, e.g., $\geq 75$ wt. %, or $\geq 90$ wt. %, with the second portion comprising at least 75 wt. % of the remainder of the total oxidant, e.g., $\geq 90$ wt. %. It is also typical for oxidant flow rate and fuel flow rate to remain substantially constant for the duration of heating mode. These flow rates are selected to achieve the desired amount of combustion heating and the desired amount of coke removal during $t_H$. The invention is compatible with conventional methods for lessening coke accumulation in thermal masses during heating mode, e.g., those described in U.S. Pat. No. 9,187,382, which is incorporated by reference in its entirety.

Other streams can be provided to the reactor during heating mode, e.g., one or more diluent streams can be provided, such as by addition to the heating mixture. When used, diluent can be provided with the oxidant and/or fuel. Suitable diluents (which can be a diluent mixture) include one or more of, e.g., oxygenate (water, carbon dioxide, etc.), non-combustible species, such as molecular nitrogen ($N_2$), and fuel impurities, such as hydrogen sulfide. For example, the oxidant can comprise 60.0 mole % to 95.0 mole % diluent and 5.0 mole % to 30.0 mole % molecular oxygen per mole of the oxidant, such as when the oxidant is air. Optionally, the oxidant has a mass ratio of diluent to molecular oxygen in the range of 0.5 to 20.0. e.g., in the range of 4.0 to 12.0.

In order to lessen or prevent the occurrence of a sharp temperature gradient in the bulk gas temperature profile at the start of pyrolysis mode and during the course of pyrolysis mode, it was expected that a relatively long-duration $t_H$ would be needed, e.g., a $t_H \geq 30$ seconds, or $\geq 50$ seconds. Surprisingly, this is not the case: a $t_H \leq 27$ seconds is typically sufficient for reheating the reactor to achieve the desired bulk gas temperature profile at the start of pyrolysis mode, e.g., $\leq 25$ second, such as $\leq 10$ seconds, or $\leq 1$ second, or $\leq 0.1$ second. For example, $t_H$ can be in the range of from 0.01 second to 25 seconds, or 0.05 second to 10 seconds, or 0.05 second to 5 seconds, or 0.05 second to 1 second.

It was also expected that fuel-oxidant combustion should be distributed through the reactor's pyrolysis zone to achieve the desired non-constant bulk gas temperature profile in the pyrolysis zone during $t_P$, and to lessen or prevent the occurrence of a sharp temperature gradient in the bulk gas temperature profile during $t_P$. Surprisingly, it has been found that this is not the case. The desired bulk gas temperature profile for pyrolysis mode is established during heating mode by carrying out fuel-oxidant combustion primarily in the central region of the reactor (e.g., a region of length L as shown in FIG. 1). While not wishing to be bound by any theory model, it is believed that concentrating combustion in the central region of the reactor leads to an improved reactor temperature profile compared to that which is achieved by distributed combustion for mainly two reasons. First, the greater fuel and oxidant flow rates needed to achieve the desired amount of combustion during $t_H$, and the resulting increased flow rate of combustion product, leads to more favorable distribution of combustion heat within the reactor. Second, during heating mode the combination of radiative heat transfer to a thermal mass proximate to the combustion zone and heat conduction within the thermal mass sufficiently moderates the reactor temperature profile so as to broaden temperature gradients in the pyrolysis zone (e.g., gradients along the length of the reactor) that would otherwise be undesirably sharp.

Referring again to FIG. 1, an appropriate combustion zone of length L can be achieved by conventional methods, e.g., by use of one or more mixer-distributors, use of a selective combustion catalyst, etc. For example, it has been found that even when mixer-distributors and selective combustion catalysts are not used, limiting Z to a value $\leq 5.0$, e.g., $\leq 3.0$, and especially $<2.0$, results in a combustion zone length L that is $\leq 50\%$ of that of the length of the pyrolysis zone, e.g., $\leq 40\%$, such as $\leq 30\%$, or $\leq 20\%$.

After the reactor is sufficiently reheated to establish the reactor temperature profile desired at the start of pyrolysis, the reactor can be switched from heating mode to pyrolysis mode, typically by decreasing or terminating fuel and oxidant flow and commencing or increasing a flow of pyrolysis feed. Representative pyrolysis feeds will now be described in more detail. The invention is not limited to these pyrolysis feeds, and this description is not meant to foreclose the use of other pyrolysis feeds within the broader scope of the invention.

Representative Pyrolysis Feeds

The pyrolysis feed comprises $C_{2+}$ hydrocarbon, e.g., $\geq 1$ wt. % of $C_{2+}$ hydrocarbon, such as $\geq 10$ wt. %, or $\geq 25$ wt. %, or ≥50 wt. %, or ≥75 wt. %, or ≥90 wt. %. Typically ≥90 wt. % of the remainder of the pyrolysis feed comprises diluent, e.g., one or more of methane, $CO_2$, water, etc. In certain aspects, the pyrolysis feed consists essentially of or even consists of $C_{2+}$ hydrocarbon, e.g., $C_2$-$C_9$ paraffinic hydrocarbon. The pyrolysis feed's hydrocarbon (the "feed hydrocarbon") generally includes any hydrocarbon compounds or mixture of hydrocarbon compounds that when subjected to the specified pyrolysis conditions produce the desired pyrolysis product. Suitable pyrolysis feeds include those disclosed in U.S. Patent Application Publication No. 2016-176781, which is incorporated by reference herein in its entirety. In certain aspects, particularly those aspects where the feed comprises ≥50 wt. % ethane (or propane, or a mixture of ethane and propane), e.g., ≥75 wt. %, such as ≥90 wt. %, conversion during pyrolysis is based on the amount of $C_{2+}$ hydrocarbon that is converted. In other aspects, e.g., those where the feed includes components such as (i) saturated $C_{4+}$ hydrocarbon and/or (ii) aromatic and/or non-aromatic cores having one or more substantially-saturated $C_{2+}$ side chains, the conversion is based on the aggregate amount of $C_{2+}$ hydrocarbon components converted, including such substantially saturated side chains as may be converted. Typically, the feed has a heat of reaction under the specified pyrolysis conditions ΔH that is ≥1000 cal./mol, e.g., ≥10,000 cal./mol, such as ≥20,000 cal./mol.

Although the feed hydrocarbon typically includes $C_{2+}$ compounds which contain hydrogen and carbon only, feed hydrocarbon can contain compounds having covalently-bound and/or non-covalently-bound heteroatoms. When present in the feed hydrocarbon, the amount of such heteroatom-containing hydrocarbon compounds is typically ≤10 wt. % based on the weight of the feed's hydrocarbon. Feed hydrocarbon that is substantially-free of non-aliphatic hydrocarbon is within the scope of the invention, as is feed hydrocarbon that is substantially free of aromatic hydrocarbon and/or substantially free of olefinic hydrocarbon, particularly $C_2$-$C_5$ olefin. Substantially-free in this context means <1 wt. % based on the weight of the feed hydrocarbon, such as ≤0.1 wt. %, or ≤0.01 wt. %, or ≤0.001 wt. %.

The feed hydrocarbon can be obtained from one or more sources of hydrocarbon, e.g., from natural hydrocarbon sources including those associated with producing petroleum, or from one or more synthetic hydrocarbons sources such as catalytic and/or non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include a recycled portion of the pyrolysis product. Such recycle, when used, can include, e.g., methane, molecular hydrogen, and $C_{2+}$ hydrocarbon, typically $C_2$ to $C_5$.

The feed hydrocarbon can include one or more of ethane, propane, butanes, saturated and unsaturated $C_6$ hydrocarbon, including those derived from one or more of Fischer-Tropsch synthesis products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$-residue admixture, naphtha-residue admixture, cracked feed, coker distillate streams, and hydrocarbon streams derived from plant or animal matter. The feed hydrocarbon can comprise volatile and non-volatile hydrocarbon, as described in U.S. Patent Application Publication No. 2016-176781. Those skilled in the art will appreciate that feed flow rate will depend on factors such as feed composition, reactor volume, pyrolysis conditions, etc. Accordingly, the invention can be carried out over a very wide range of feed flow rates, e.g., at a flow rate ≥0.001 kg/s, such as ≥0.1 kg/s, or ≥10 kg/s, or ≥100 kg/s, or more.

Although the invention is not limited thereto, the specified process can be used for upgrading relatively refractory light (e.g., $C_2$-$C_5$) paraffinic hydrocarbon, such as ethane. Accordingly, the feed hydrocarbon can comprise ethane in an amount ≥1 wt. %. e.g., ≥5 wt. %, such as ≥10 wt. %. Suitable feeds include those comprising ≥50 wt. % ethane, such as ≥75 wt. %, or ≥90 wt. %, or ≥95 wt. %. For example, the feed can comprise an amount of ethane in the range of from 1 wt. % to 99 wt. %, such as 5 wt. % to 95 wt. %, or 10 wt. % to 90 wt. %. One representative feed hydrocarbon comprises (i) ≥10 wt. % ethane, or ≥50 wt. %, or ≥90 wt. %, such as in the range of from 10 wt. % to 99.5 wt. % ethane, with ≥95 wt. % of the balance of the feed hydrocarbon comprising one or more of methane, propane, and butanes. In other aspects, the feed comprises ≥90 wt. % of (i) ethane and/or (ii) propane. The light paraffinic hydrocarbon can be provided from any convenient source, e.g., from synthetic and/or natural sources. Light paraffinic hydrocarbon ethane can be provided from petroleum or petrochemical processes and/or sources of geological origin, e.g., natural gas. In particular aspects, the pyrolysis feed comprises ≥90 wt. % of (i) ethane and/or (ii) propane.

The pyrolysis feed optionally includes diluent, typically comprising compositions that are essentially non-reactive under the specified pyrolysis conditions, such as one or more of methane, water (e.g., steam), hydrogen, nitrogen and the noble gases, such as helium, neon and argon. Diluent present in the pyrolysis feed's source (e.g., methane and/or $CO_2$ present in natural gas) and diluent added to the pyrolysis feed are within the scope of the invention. Diluent, when present, is typically included in the pyrolysis feed in an amount ≤60 wt. % based on the weight of the feed, e.g., ≤50 wt. %, such as ≤40 wt. %, or ≤30 wt. %, or ≤20 wt. %, or ≤10 wt. %, or in the range of from 1 wt. % to 50 wt. %. Diluent is also suitable for use as a sweep gas, e.g., for (i) removing at least a portion of any deposits in the reactor after the pyrolysis mode and/or after heating mode and/or (ii) adjusting the reactor's temperature profile—heat carried by the sweep gas from warmer regions of the reactor for transfer to cooler regions will increase the temperature of the cooler regions and further lessen or prevent sharp gradients in the reactor temperature profile.

A flow of the pyrolysis feed is conducted to the pyrolysis reactor during pyrolysis mode, typically in a reverse-flow direction, e.g., one that is opposed to that of oxidant flow. During pyrolysis mode, at least a portion of the feed hydrocarbon is pyrolysed to produce a desired pyrolysis product. Certain pyrolysis conditions that are useful for pyrolysing the specified pyrolysis feeds will now be described in more detail. The invention is not limited to these pyrolysis conditions, and this description is not meant to foreclose the use of other pyrolysis conditions within the broader scope of the invention.

Representative Pyrolysis Mode Conditions

When heating mode is carried out under the specified conditions, the bulk gas temperature profile at the start of pyrolysis mode continuously varies over the length of the pyrolysis zone. $T_{av}$ decreases during $t_P$, but the amount of decrease is ≤100° C. $T_P$ also decreases during the course of the pyrolysis, but its position along the length of the pyrolysis zone and the general shape of the bulk gas temperature profile typically remain substantially the same during $t_P$. $T_{av}$ (and typically $T_P$) decreases during $t_P$ by ≤100° C. during the course of the pyrolysis, e.g., by ≤75° C., such as by ≤50° C., or by ≤25° C., or by ≤10° C., or by ≤5° C. In certain aspects, e.g., those where $T_P$ is located downstream of the first thermal mass, the bulk gas temperature proximate to the downstream end of the first thermal mass decreases by 100° C. during the course of the pyrolysis, e.g., ≤75° C., such as ≤50° C., or ≤25° C., or ≤10° C., or ≤5° C. Regions of substantially-constant temperature along the length of the pyrolysis zone are avoided. Sharp gradients in the bulk gas temperature profile within the pyrolysis zone are also substantially avoided. Although high-severity pyrolysis conditions can be used, it is typical to use low severity conditions.

It has been found that the pyrolysis can be carried out within these thermal limitations, e.g., within the specified decrease for $T_{av}$ and $T_P$, for a wide range of thermal mass OFA and a wide range of pyrolysis conditions by selecting a pyrolysis mode duration $t_P$ to be no greater than a reference time duration $t_{ref}$, where $t_{ref}$ is determined from the equation:

$$t_{Ref} = (t_R * \rho_s * C_p * R * T_{av} * \Delta T_{av}) * ([1-OFA]*OFA^{-1}) * (X * \Delta H * P)^{-1}. \quad (II)$$

In evaluating equation II, $\Delta H$ is the pyrolysis feed's heat of reaction under the pyrolysis conditions, e.g., ≥20,000 cal./mol.; $t_R$ is the residence time in the channel during the pyrolysis, e.g., $t_R$ ≤1 Sec.; X is the conversion of the feed to the pyrolysis, e.g., X ≥50%; P is the average total pressure in the channel during the pyrolysis, e.g., P ≥1 bar; $T_{av}$ is the average bulk gas temperature in the channel at the start of the pyrolysis, e.g., $T_{av}$ ≤1500° C. at the start of pyrolysis; $\Delta T_{av}$ is the change (typically a decrease) in average bulk gas temperature during $t_P$; OFA is ≤55%; and R is substantially equal to the feed's Gas Constant, which can generally be approximated with sufficient accuracy under the specified pyrolysis conditions by the Ideal Gas Constant. It can be the case that $t_{ref}$ corresponds to a time that is too short to be achieved with equipment available for use in switching the flows of feeds and products as needed when transitioning from pyrolysis mode to heating mode, and vice versa. In these cases, $t_P$ is selected to be the minimum pyrolysis time duration achievable with available flow control equipment. For example, if the minimum pyrolysis time duration achievable with available flow control equipment is 0.001 seconds, then for $t_{ref}$ is ≥0.001 sec, $t_P$ is ≤$t_{ref}$ and for $t_{ref}$ ≤0.001 sec., $t_P$ is 0.001 sec.

Typically, $t_{ref}$ is ≥0.001 sec., e.g., ≥0.01 sec., such as ≥0.1 sec., or ≥1 sec., or ≥10 sec. Accordingly, $t_P$ can be of relatively long duration. e.g., ≥1 second, such as ≥2 seconds, or ≥5 seconds, or ≥10 seconds, or ≥20 seconds, or ≥30 seconds, or even ≥1 minute or more. For example, $t_P$ can be in the range of from 1 second to 30 seconds, e.g., 2 seconds to 15 seconds, such as 2 seconds to 10 seconds. Conventional methods can be used to achieve these ranges of $t_P$, e.g., using one or more poppet valves and/or hydrodynamic valving, but the invention is not limited thereto. The bulk gas temperature profile typically maintains a substantially constant shape (although decreasing in magnitude) during these relatively long $t_P$ values. Using a $t_P$ ≥2 seconds and the specified OFA lessens the appearance of pyrolysis zone segments having a substantially-constant bulk gas temperature profile. Using these $t_P$ values and the specified OFA also substantially prevents relatively sharp temperature gradients in the pyrolysis zone. For example, at any time during the pyrolysis variations in the bulk gas temperature are typically ≤140° C. within any pyrolysis zone segment having a length ≤10% of $l_C$, e.g., ≤100° C., such as ≤50° C.

The pyrolysis conditions in the pyrolysis zone during $t_P$ generally include $T_P$ ≤1400° C., $T_{av}$ ≤1200° C., and an average total pressure (e.g., within the channel of the first thermal mass) ≥100 kPa. Gas residence time in the pyrolysis zone (e.g., feed residence time when the feed is substantially non-liquid during the pyrolysis) is generally ≤0.4 seconds to decrease the conversion to coke of desired products such as light olefin. Typically, the pyrolysis conditions include $T_P$ ≤1200° C., e.g., ≤1100° C., such as ≤1000° C. or in the range of from 1000° C. to 1400° C.; $T_{av}$ ≤1100° C., e.g., ≤1000° C., such as ≥900° C., or in the range of from 900° C. to 1100° C., or 925° C. to 1075° C.; and a feed hydrocarbon partial pressure ≥7 psia (48 kPa), or ≥10 psia (69 kPa), or ≥20 psia (138 kPa), or ≥30 psia (207 kPa). The average total pressure is typically ≥5 psig (34 kPag), or ≥15 psig (103 kPag), or ≥40 psig (276 kPag), or ≥80 psig (552 kPag), or ≥120 psig (827 kPag). Particularly when the pyrolysis feed includes diluent, the average total pressure can be ≥150 psig (1034 kPag), or ≥300 psig (2068 kPag), or ≥500 psig (3447 kPag). Gas residence time in the pyrolysis zone is typically ≤0.2 second; preferably ≤0.15 second or ≤0.1 second; or in the range of 0.001 second to 0.4 second, or in the range of 0.01 second to 0.4 second, or in the range of 0.01 second to 0.2 second. For example, the pyrolysis feed can be passed through thermal mass 1 at a gas residence time at a bulk gas temperature ≥800° C. that is ≤0.100 second, such as ≤0.060 second, such as ≤0.040 second, or in the range of 0.001 second to 0.100 second, or in the range of 0.002 second to 0.060 second, or in the range of 0.002 second to 0.040 second. When utilizing a first thermal mass having an OFA in the specified range, these conditions have been observed to decrease $T_P$ and/or $T_{av}$ by ≤100° C., e.g., ≤75° C., such as ≤50° C., or ≤25° C. or ≤10° C., or ≤5° C., for a $t_P$ ≥1 second, e.g., ≥2 seconds, such as ≥5 seconds, or ≥10 seconds, or ≥20 seconds, or ≥30 seconds, or even ≥1 minute or more.

Carrying out the pyrolysis at a $t_P$ ≤$t_{ref}$ under the specified conditions in a reactor having the specified channeled thermal mass has been found to moderate variations in $T_P$ and Tar during $t_P$ even at relatively high pyrolysis temperatures, which in turn moderates variations in the yield of less desirable pyrolysis products such as acetylene and coke. These desirable effects can be achieved under the specified conditions even at a relatively long $t_P$. e.g., a $t_{ref}$ of 1 seconds, which encompasses a commercially-reasonable range of $t_P$. This in turn leads to a simplification of olefin purification and recovery facilities.

It has also been found that when $T_{av}$ in the channel exceeds 900° C., it is beneficial for $\Delta T_{av}$ to be ≤50° C. when $T_{av}$ in the channel exceeds 1000° C., it is beneficial for $\Delta T_{av}$ to be ≤40° C., and when $T_{av}$ in the channel exceeds 1100° C., it is beneficial for $\Delta T_{av}$ to be ≤20° C. Parameters $t_P$ and OFA can be optimized in commercially-desirable ranges to achieve these conditions of $T_{av}$ and $\Delta T_{av}$ using the relationship $$([OFA-1]/[t_P * OFA]) = (t_R * \rho_s * C_p * R * T_{av} * \Delta T_{av})^{-1} * (X * \Delta H * P). \quad (III)$$

Although using this relationship may find its greatest utility when $T_{av}$ exceeds 900° C., its use can be advantageous when optimizing OFA and $t_P$ at other values of $T_{av}$. When evaluating equation III, $\Delta H$ is the pyrolysis feed's heat of reaction under the pyrolysis conditions, e.g., ≥20,000 cal./mol.; $t_R$ is the residence time in the channel during the pyrolysis, e.g., $t_R$ ≤1 sec.; X is the conversion of the feed to the pyrolysis, e.g., X ≥50%; P is the average total pressure in the channel during the pyrolysis, e.g., P ≥1 bar; Tar is the average bulk gas temperature in the channel during the pyrolysis, e.g., $T_{av}$ ≤1500° C.; $\Delta T_{av}$ is the change in average bulk gas temperature in the channel; OFA is the open frontal area of the channeled thermal mass, e.g., an OFA in the range of from 10% to 55%, e.g., 10% to 50%, such as 10% to 45%, or 10% to 35%; and R is substantially equal to the feed's Gas Constant, which can generally be approximated with sufficient accuracy under the specified pyrolysis conditions by the Ideal Gas Constant.

Thermal profiles resulting from using the specified regenerative reactor having a thermal mass of the specified OFA for a pyrolysis mode having the specified time duration $t_P$ will now be described in more detail with respect to FIGS. 2 and 3. As shown in the figures. $\Delta T_P$ is a positive number corresponding to the change in $T_P$ during $t_P$.

FIG. 2 schematically shows a representative regenerative reverse-flow reactor, similar to that shown in FIG. 1, and representative gas temperature profiles during pyrolysis. The solid line represents the bulk gas temperature profile at the start of $t_P$, and the dashed line represents the bulk gas temperature profile at the end of $t_P$. At the start of $t_P$, the flow of combustion mixture 19 is curtailed a flow of pyrolysis feed 15 is established. The reactor's pyrolysis zone at the start of $t_P$ encompasses the region between apertures 5 and 11, the shaded region 16 of thermal mass 7, and the shaded region 14 of thermal mass 1. Particularly at relatively large flow rates of fuel and/or oxidant during heating mode, and/or when $t_H$ is of relatively long duration, the peak gas temperature $T_P$ during $t_P$ can be displaced away from the aperture 11, toward aperture 5 or beyond. In such aspects, the length of the pyrolysis zone's downstream segment $l_B$ is less than that of the upstream segment $l_A$, e.g., at least 10% less, such as at least 25% less, or at least 50% less. The total length of the pyrolysis zone $l_C$ is the sum of $l_A$ and $l_B$. Typically, $l_C$ is in the range of from 10% to 50% of the total length of reactor 50, e.g., in the range of 20% to 40%. For example, $l_C$ can be in the range of from 20% to 40% of $L+L_2+L_3+L_4$ (FIG. 2). The locations of the terminal ends of $l_A$ and $l_B$ (the locations where the first and second heat transfer zones abut the pyrolysis zone during pyrolysis mode) are determined by $T_{MIN}$.

FIG. 2 shows aspects where $T_P$ is located within shaded region 14 of thermal mass 1. Other aspects of the invention are schematically illustrated in FIG. 3. In these aspects, a mixer-distributor 10 is located within the combustion zone. In FIGS. 1-3, components and streams performing similar functions have the same index number.

In the aspect of FIG. 3, the bulk gas temperature profile at the start of pyrolysis mode (profile $PR_3$) exhibits at least two local maxima, as does profile $PR_4$ which represents the bulk gas temperature profile at the end $t_P$. While not wishing to be bound by any theory or model, it is believed that the bi-modal bulk gas temperature profile results from heat radiated from the mixer distributor during heating mode toward thermal masses 1 and 7. Since the end of the mixer-distributor opposite aperture 5 achieves a greater temperature than the end facing aperture 11 during heating mode, and since radiative heating is a relatively short-range phenomena (the inverse-square law applies), thermal mass 1 is heated more than thermal mass 7. The resultant bulk gas temperature profile $PR_3$ at the start of pyrolysis mode is therefore believed to be a substantially linear combination of bulk gas temperature profile $PR_1$, which is related to the heating of thermal mass 7, and bulk gas temperature profile $PR_2$, which is related to the heating of thermal mass 1. Greater fuel-oxidant flow rates during heating mode lead to additional heating of thermal mass 1, e.g., by convective heat transfer from the combustion product, which displaces the peak temperature of profile $PR_2$ toward (or even into) shaded region 14. The maximum gas temperature of profile $PR_1$ is typically 20% to 70% of the maximum gas temperature of profile $PR_2$, such as 30% to 70%.

In aspects such as those illustrated in FIGS. 2 and 3, the pyrolysis conditions include a bulk gas temperature profile during pyrolysis (i.e., the profile of the pyrolysis bulk gas temperature) which at the start of $t_P$ increases substantially monotonically from a first temperature ($T_1$) proximate to aperture 3 of thermal mass 1 to temperature $T_{MIN}$ proximate to a location (the reference location) where the first heat transfer zone abuts the pyrolysis zone, e.g., reference location $R_1$ at the start of $t_P$ and reference location $R_2$ at the end of $t_P$. The peak gas temperature $T_P$ is greater than $T_{MIN}$ at the start of $t_P$, and is ≥$T_{MIN}$ at the end of $t_P$. $T_P$–$T_{MIN}$ at the start of pyrolysis is typically in the range of from 10° C. to 400° C., or 25° C. to 300° C., or 50° C. to 200° C. $T_v$, is typically ≥$T_{MIN}$+10° C. at the start of $t_P$. For example, $T_{av}$–$T_{MIN}$ at the start of pyrolysis is typically in the range of from 5° C. to 200° C., or 10° C. to 150° C. or in a range of from 20° C. to 100° C., or from 25° C. to 75° C. Typically, the position of $T_P$ within the pyrolysis zone remains substantially constant during the pyrolysis. Substantially constant in this context means that the location of $T_P$ changes during pyrolysis mode from its initial position by ≤+/−20% of $l_c$, e.g., ≤+/−15%, such as ≤+/−10%, or typically ≤+/−5%. Unlike $T_P$, the reference location typically varies in position during $t_P$. $T_1$ is typically less than $T_{MIN}$ during $t_P$, in other words, at least a segment of first thermal mass 1 is included in the first heat transfer zone. The value of $T_{MIN}$ depends on several factors, e.g., the choice of feed and pyrolysis process conditions such as pressure and residence time. For feeds comprising light hydrocarbon, e.g., one or more $C_2$-$C_5$ paraffin, $T_{MIN}$ at the start of $t_P$ is typically ≤1400° C., e.g., ≤1300° C., such as ≤1200° C., or ≤1100° C. or ≤1000° C. For example, at the start of $t_P$, $T_{MIN}$ is typically in the range of from 700° C. to 1200° C., e.g., 975° C. to 1100° C., and $T_P$ is typically ≥1150° C. $T_{MIN}$–$T_1$ at the start of pyrolysis is typically in the range of from 10° C. to 400° C., or 25° C. to 300° C., or 50° C. to 200° C. In particular aspects utilizing a feed comprising ethane and/or propane, the pyrolysis conditions at the start of $t_P$ typically include $T_1$≥900° C., e.g., ≤750° C., such as ≤500° C., or ≤400° C., or in the range of from 350° C. to 800° C.

At the start of $t_P$, feed conversion typically exhibits a profile (not shown in FIGS. 2 and 3) which increases from a first conversion ($X_1$) at a reference location $R_1$ positioned between the first and second apertures to a second conversion ($X_2$) proximate to aperture 5, wherein $X_1$ is in the range of from 25% to 85%, and $X_2$ is in the range of 65% to 98%. Reference location $R_1$ is typically proximate to the location where the terminal end of the pyrolysis zone abuts the first heat transfer zone at the start of $t_P$. The peak gas temperature decreases during $t_P$, but the bulk gas temperature profile typically maintains substantially the same shape as shown. Although the bulk gas temperature profile (within the pyrolysis zone) at the start of $t_P$ is typically substantially congruent with that at the end of $t_P$, the location in the pyrolysis zone at which conversion $X_1$ is achieved translates during $t_P$ from $R_1$ toward aperture 5 to reference position $R_2$ at the end of $t_P$. In particular aspects where the feed comprises ethane and/or propane, the process can include one or more of (i) $X_1$ in the range of from 25% to 60%, (ii) the bulk gas temperature proximate to aperture 5 is in the range of from 1025° C. to 1075° C., (iii) $X_2$ in the range of from 85% to 98%, (iv) $T_{MIN}$ in the range of from 900° C. to 1000° C. and (v) the reference location $R_1$ is positioned within $0.2*L_1$ and $0.4*L_1$ of aperture 5. More particularly, conditions at the start of the pyrolysis can include (i) an acetylene selectivity in a range of from 0% to 1% at the reference location, which acetylene selectivity increases, e.g., monotonically, to a range of 5% to 10% at the second aperture, (ii) an ethylene selectivity in a range of from 85% to 95% at the reference location, which ethylene selectivity decreases, e.g., monotonically, to a range of 70% to 85% at the second aperture, (iii) a propylene selectivity in a range of from 0.7% to 0.9% at the reference location, which propylene selectivity varies monotonically or non-monotonically to a range of 0.4% to 0.6% at the second aperture, and (iv) a benzene selectivity (corresponding to selectivity for coke and coke precursors) in a range of from 0.005% to 1.5% at the reference location, which butadiene selectivity increases, e.g., monotonically, to a range of 4% to 5% at the second aperture.

By modulating bulk gas temperature over the length of the pyrolysis zone during pyrolysis mode, the pyrolysis product conducted away from the reactor comprises a range of desired hydrocarbon products, including a desirable range of $C_2$-$C_5$ olefin. Typically, one or more of the desired hydrocarbon compounds is separated from the pyrolysis product, e.g., for storage and/or further processing. For example, one or more of ethylene, propylene, butadiene butenes, etc. can be separated from the pyrolysis product, e.g., for recovery and use in producing products such as fuels and fuel additives, oxygenates, polymer, etc. Molecular hydrogen and methane can be separated and recovered from the pyrolysis product, e.g., as a tail gas. Light paraffinic hydrocarbon can be separated recovered, e.g., for use as a fuel, such as a fuel for heating mode. Conventional separations and recovery methods can be used, e.g., those described in U.S. Patent Application Publication No. 2016-176781, but the invention is not limited thereto. Since OFA and/or $t_P$ are selected so that $T_P$ or $T_{av}$ (and typically both) decrease by ≤100° C. during the course of the pyrolysis, e.g., ≤75° C., such as ≤50° C., or ≤25° C., or ≤10° C., or ≤5° C., yields of these desired products typically do not vary appreciably as a function of time during the course of the pyrolysis, leading to a considerable simplification of product recovery systems over conventional processes.

Certain representative pyrolysis products will now be described in more detail. The invention is not limited to these products, and this description is not meant to foreclose the production of other pyrolysis products within the broader scope of the invention.

Representative Pyrolysis Products

In certain aspects, the pyrolysis product conducted away from the reactor is primarily gaseous and comprises molecular hydrogen; methane; ethane; ethylene; propane; propylene; butanes; butenes; butadiene; $C_5$ hydrocarbon, including normal, iso, and cyclo $C_5$ olefin and paraffin, and $C_{6+}$ hydrocarbon, including aromatics and normal, iso, and cyclo $C_{6+}$ olefin and paraffin. For example, when utilizing one representative pyrolysis feed comprising light paraffinic hydrocarbon and representative heating mode and pyrolysis mode conditions, the pyrolysis product can comprise 2 wt. % to 10 wt. % methane, 50 wt. % to 95 wt. % ethylene, 0.2 wt. % to 1 wt. % propylene, 0.1 wt. % to 5 wt. % butadiene, and up to about 3 wt. % benzene, based on the weight of the pyrolysis product. As may be appreciated, these very desirable compositional ranges for the identified hydrocarbon compounds are achieved not only at the start of pyrolysis mode, but during the duration of $t_P$. This stands in sharp contrast to conventional processes operating at a gas temperature ≤1200° C., such as steam cracking, since these operate with little temperature variation in the pyrolysis zone, and produce a pyrolysis product having very narrow compositional ranges for the desired hydrocarbon compounds.

Example

In this prophetic example, a pyrolysis feed consisting essentially of ethane is exposed to the specified pyrolysis conditions in a representative reverse-flow reactor configured to be similar to the one illustrated in FIG. 1. Thermal mass 1 is a refractory honeycomb having a $C_p$ of 0.21 (cal./(g ° C.)) and a solid density $\rho_s$ of 3.9 g/cm³. The reactor's thermal profile at the start of $t_P$ is similar to that shown in FIG. 2, with predetermined pyrolysis conditions of $T_{av}$ of about 800° C., a gas residence time of 0.1 sec., a heat of reaction $\Delta H$ of 32740 cal./mole, an average conversion X of 70%, and an average total pressure P of 2.7 bar.

Figure 4:
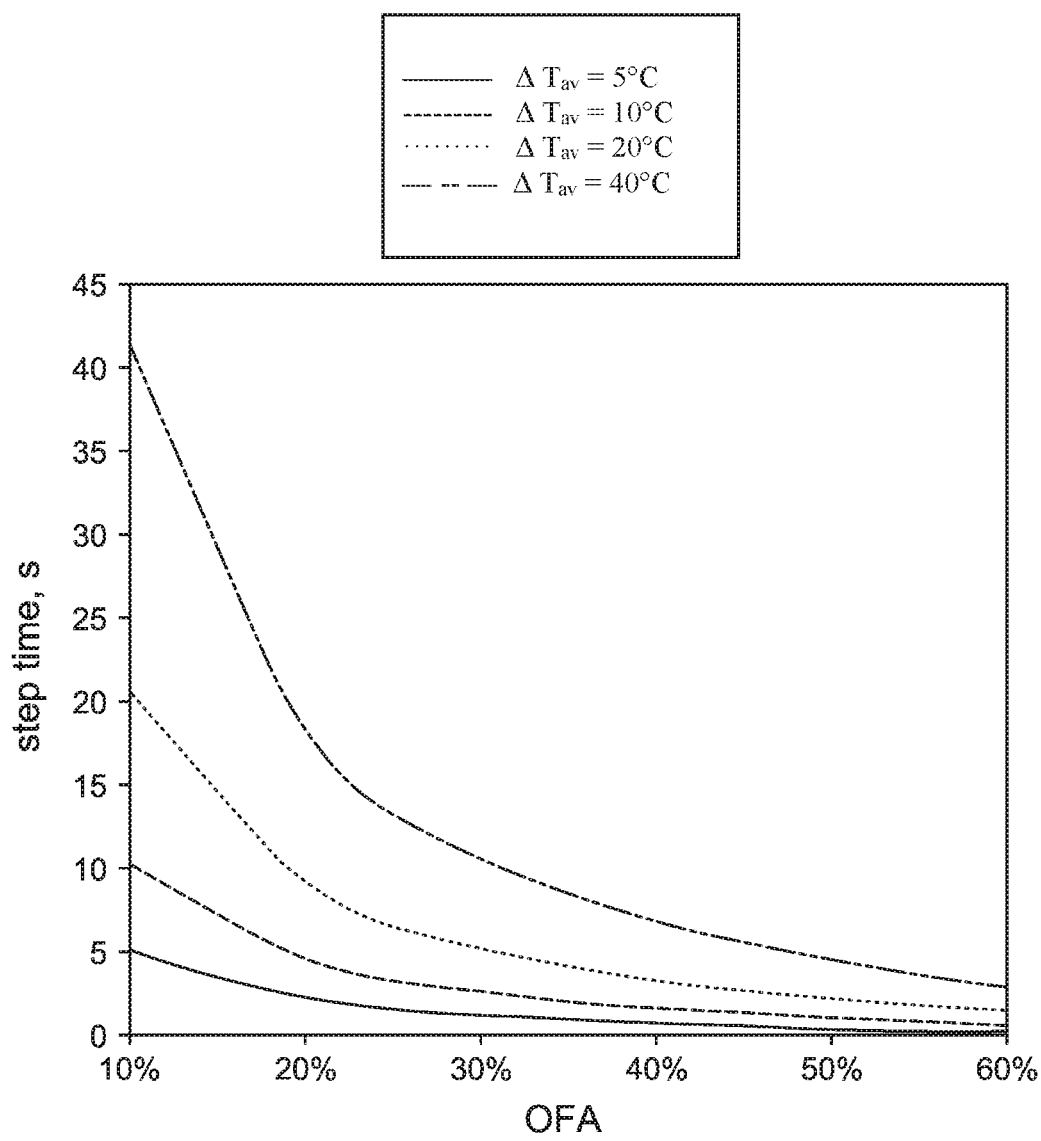
FIG. 4 shows the variation of conversion of pyrolysis step time with OFA in a representative aspect.

Equation III is used to determine values for $t_P$ and OFA under these predetermined conditions at four values of $\Delta T_{av}$ equal to 5° C., 10° C., 20° C., and 40° C. The results are plotted in FIG. 4. As shown in the figure, OFA can be optimized in a commercially desirable range of about 25% to about 45% while simultaneously optimizing $t_P$ in a commercially desirable range of about 1 sec. to about 12 sec. to achieve a desirable $\Delta T_{av}$ under the predetermined conditions.

Figure 5:
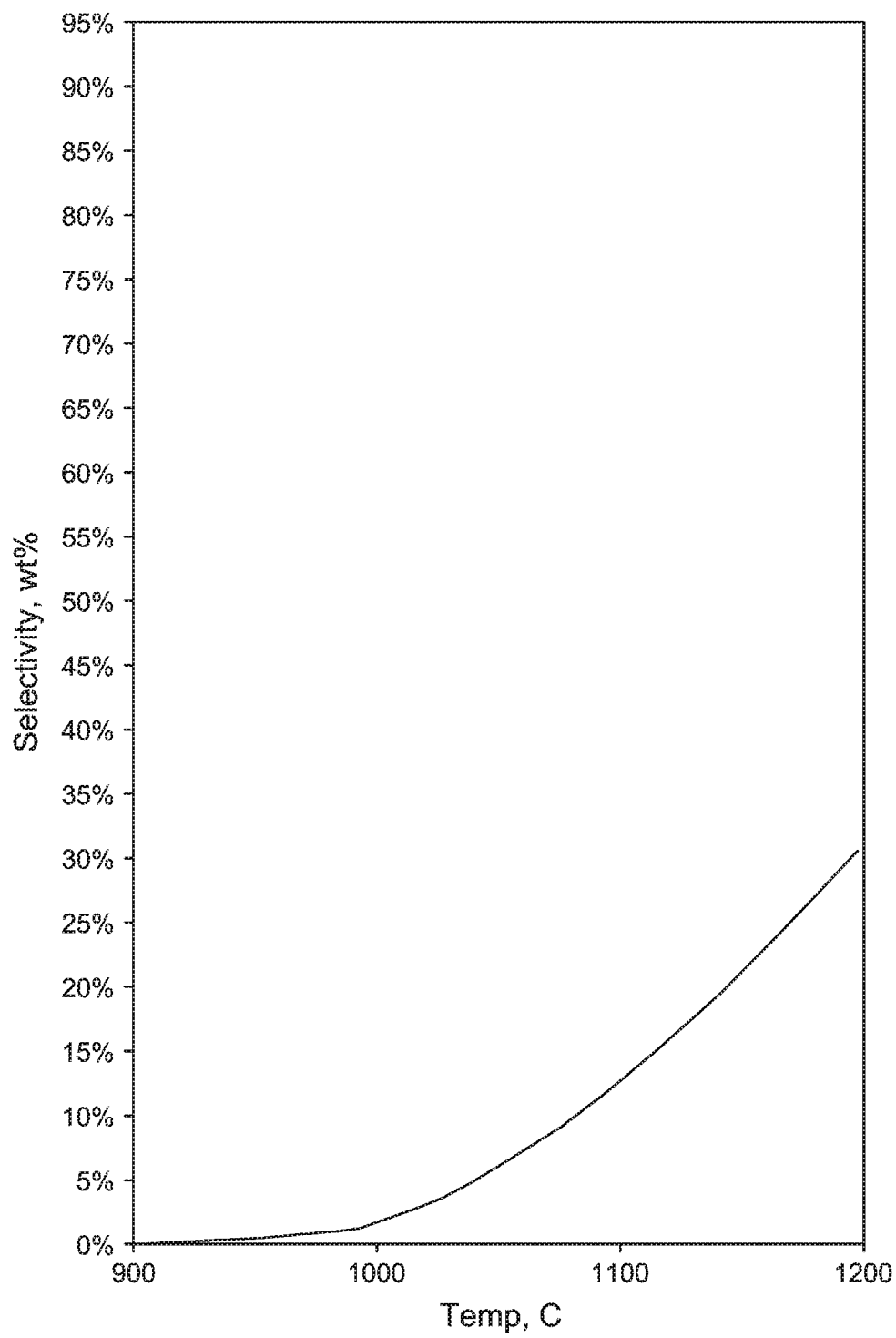
FIG. 5 shows the variation of acetylene selectivity as a function of $T_{av}$ in a representative aspect.
Figure 6:
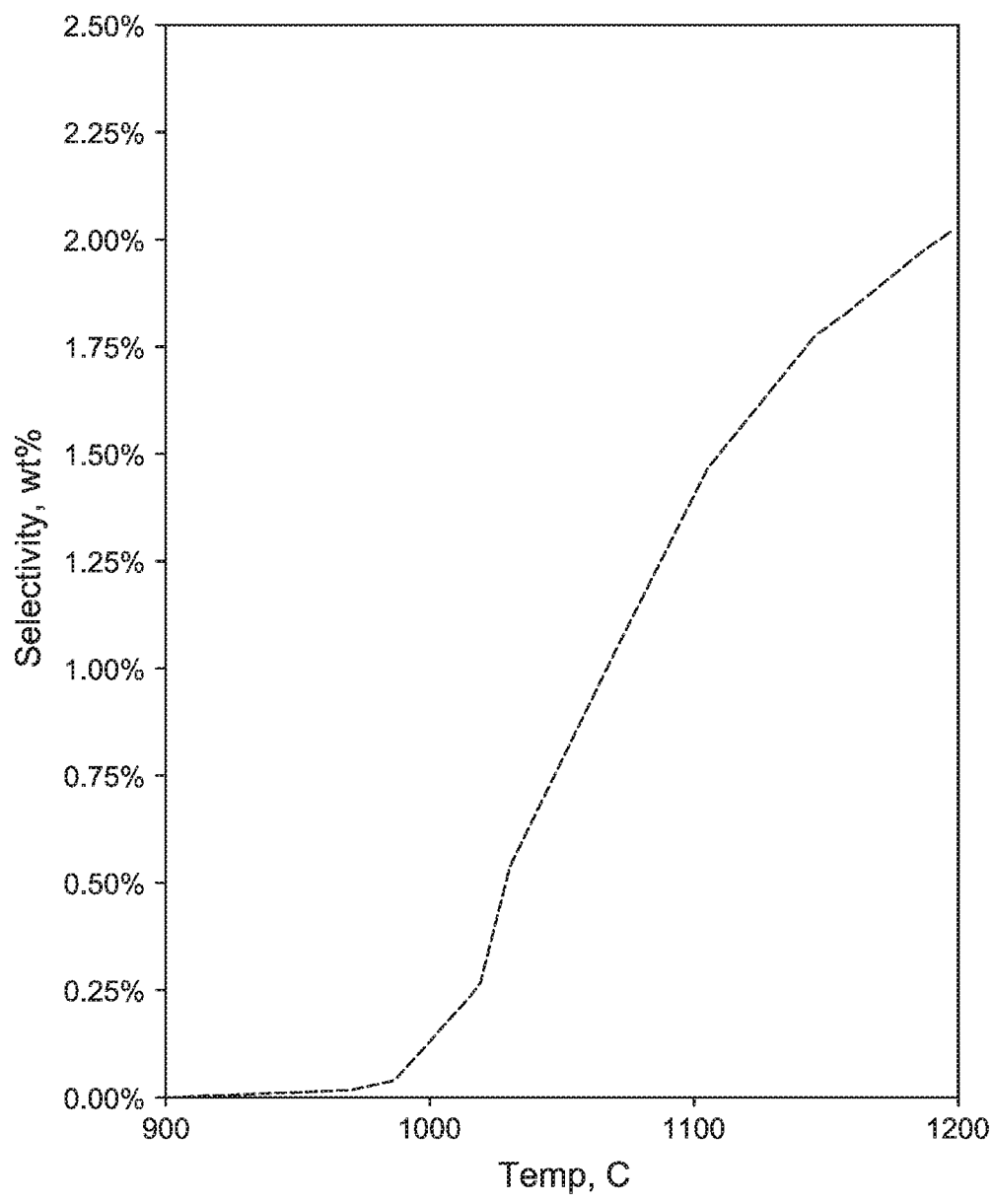
FIG. 6 shows the variation of benzene selectivity as a function of $T_{av}$ in a representative aspect.

Certain benefits of carrying out the optimization are illustrated in FIG. 5 and FIG. 6. As shown, variation in selectivity to acetylene (FIG. 5) is ≤1 wt. % and variation in the selectivity of a representative coke precursor (benzene, FIG. 6) is ≤0.1 wt. % as $T_{av}$ decreases from about 900° C. at the start of $t_P$ to about 960° C. at the end of $t_P$ ($\Delta T_{av}$ of 40° C.).

All patents, test procedures, and other documents cited herein, including priority documents, are fully incorporated by reference to the extent such disclosure is not inconsistent. It is not intended that the scope of the claims appended hereto be limited to the descriptions set forth herein but rather that the claims be construed as encompassing all patentable features which reside herein, including all features which would be treated as equivalents thereof by those skilled in the relevant art. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa. All pressures are absolute (kPa, psia, bar) except where gauge pressure (kPag, psig, barg) is expressly indicated.

The invention claimed is:

1. A hydrocarbon pyrolysis process, the process comprising:
   (a) providing a feed comprising ≥1 wt. % of $C_{2+}$ hydrocarbon, wherein the feed has a pyrolysis heat of reaction ($\Delta H$ in cal./mol);

(b) providing an elongated flow-through reactor having (i) an internal volume which includes first and second regions, opposed first and second openings in fluidic communication with the internal volume, wherein the first and second openings are separated by a reactor length ($L_R$), and (ii) a first thermal mass located in the first region, wherein the first channeled thermal mass has a solid density ($\rho_s$) ≤12 g/cm$^3$, a heat capacity ($C_P$) ≤0.5 cal/g° C., and an open frontal area (OFA) ≤55%, and wherein the first channeled thermal mass includes:
  (A) a first aperture, the first aperture being proximate to the first opening and in fluidic communication with the first opening,
  (B) at least one internal channel in fluidic communication with the first aperture, and
  (C) a second aperture, the second aperture being in fluidic communication with the first aperture via a flowpath through the channel;
(c) preselecting pyrolysis conditions for pyrolysis of the feed in the channel, wherein the pyrolysis conditions include a residence time in the channel ($t_R$) ≤1 sec., a feed conversion (X) ≥50%, an average total pressure in the channel (P) ≥1 bar, an average bulk gas temperature in the channel ($T_{av}$) ≤1500° C. at the start of the pyrolysis, a peak gas temperature ($T_P$) located in the channel, $T_P > T_{av}$, and a change in average bulk gas temperature during the pyrolysis ($\Delta T_{av}$) ≤100° C.;
(d) predetermining a reference pyrolysis step time ($t_{ref}$), wherein $$t_{ref} = (t_R * \rho_s * C_p * R * T_{av} * \Delta T_{av}) * ([1-OFA] * OFA^{-1}) * (X * \Delta H * P)^{-1},$$

and R is substantially equal to the feed's Gas Constant; and
(e) pyrolysing the feed in the channel under the preselected conditions during a pyrolysis time interval $t_P$ that does not exceed $t_{Ref}$.

2. The process of claim 1, wherein (i) the location of $T_P$ remains substantially constant during $t_P$, (ii) the feed is introduced into the reactor through the first opening, through the first aperture, and toward the second aperture at a flow rate ≥0.01 kg/s, (iii) when $t_{ref}$ is >0.001 second, $t_P$ is ≤$t_{ref}$, and when $t_{ref}$ is ≤0.001 second, $t_P$ is 0.001 second, and (iv) the process further comprises:
  (f) at least part of the pyrolysis of the feed flow's $C_{2+}$ hydrocarbon is carried out in the channel, which cools the first channeled thermal mass and produces a flow of a pyrolysis product comprising molecular hydrogen, acetylene, $C_{2+}$ olefin, and coke; and
  (g) during $t_P$, conducting the flow of at least a portion of the pyrolysis product into the second region of the internal volume via the second aperture, and away from the reactor via the second opening.

3. The process of claim 1, wherein the pyrolysis conditions further include a hydrocarbon partial pressure of ≥7 psia (48 kPa) and an average total pressure of ≥5 psig (34 kPag), and (v) $t_P$ is ≥2 seconds.

4. The process of claim 1, wherein (i) the reactor is a reverse-flow thermal pyrolysis reactor, the reactor further comprising a second thermal mass located in the second region of the internal volume, the second thermal mass having at least one internal channel having at least one in fluidic communication with the internal channel of the first thermal mass, and (ii) the process further comprises (f) conducting the pyrolysis product through the internal channel of the second thermal mass before the pyrolysis product is conducted away from the reverse-flow reactor, and (g) cooling the pyrolysis product by transferring heat from the pyrolysis product to the second thermal mass.

5. The process of claim 1, wherein (i) the $C_{2+}$ olefin includes one or more of ethylene, propylene, and butylene, (ii) the pyrolysis product further comprises coke and one or more of acetylene, benzene, methane, and at least a portion of any unconverted feed, and (iii) at least a portion of the coke remains in the internal channel of the first thermal mass as a deposit.

6. The process of claim 1, wherein the feed comprises one or more of ethane, propane, butanes, saturated and unsaturated $C_6$ hydrocarbon, including those derived from one or more of Fischer-Tropsch synthesis products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$-residue admixture, naphtha-residue admixture, cracked feed, coker distillate streams, and hydrocarbon streams derived from plant or animal matter.

7. The process of claim 1, wherein X is ≥60 wt. %.

8. The process of claim 1, wherein (i) the OFA ≤50%, and (ii) $\Delta T_{av}$ 75° C.

9. The process of claim 1, wherein (i) $t_P$ is ≥2 seconds, (ii) the pyrolysis conditions include a gas residence time in the channel of ≤0.5 seconds, (iii) the feed flow rate is (A) substantially constant during $t_P$ and (B) ≥0.1 kg/s, (iv) the OFA is in the range of from 10% to 50%; (v) the first thermal mass has a thermal conductivity in the range of from 0.5 W/m° K to 50 W/m° K, a coefficient of thermal expansion in the range of from $1 \times 10^{-7}$/° K to $2 \times 10^5$/° K, an average wetted surface area per unit volume in the range of from 1 cm$^{-1}$ to 100 cm$^{-1}$, an average wetted surface area per unit volume in the range of from 1 cm$^{-1}$ to 100 cm$^{-1}$; (vi) the internal channel of the first thermal mass includes a plurality of substantially parallel passages and has a passage density in the range of from 77000/m$^2$ to $1.3 \times 10^6$/m$^2$; (vii) the refractory has a specific heat capacity at 300° K ≥0.04 [kj/(° K kg)] and a mass density ≥3000 kg/m$^3$; and (vii) the refractory includes at least one oxide of one or more elements selected from Groups 2-14 of the Periodic Table.

10. The process of claim 9, wherein the first thermal mass is in the form of at least one monolithic honeycomb having a mass ≥1 kg; the refractory's oxide includes oxide of at least one of Al, Si, Mg, Ca, Fe, Mn, Ni, Co, Cr, Ti, Hf, V, Nb, Ta, Mo, W, Sc, La, Yt, Zr, and Ce; the refractory's specific heat capacity at 300° K is in the range of from 0.04 [kj/(° K kg)] to 1.2 [kj/(° K kg)]; the refractory's mass density is in the range of from 3000 kg/m$^3$ to 5000 kg/m3; and $t_R$ is in the range of from 0.01 second to 0.4 second.

11. A hydrocarbon pyrolysis process, the process comprising:
  (a) providing a feed comprising ≥1 wt. % of $C_{2+}$ hydrocarbon, wherein the feed has a pyrolysis heat of reaction ($\Delta H$ in cal./mol);
  (b) providing an elongated flow-through reactor having (i) an internal volume which includes first and second regions, (ii) opposed first and second openings in fluidic communication with the internal volume, wherein the first and second openings are separated by a reactor length (L), and (iii) a thermal mass located in the first region, wherein the thermal mass has a solid density ($\rho_s$) ≤12 g/cm$^3$, a heat capacity ($C_P$) ≤0.5 cal/g° C., and a predetermined open frontal area (OFA), and wherein the thermal mass includes:
  (A) a first aperture, the first aperture being proximate to the first opening and in fluidic communication with the first opening,
  (B) at least one internal channel in fluidic communication with the first aperture, and
  (C) a second aperture, the second aperture being in fluidic communication with the first aperture via a flowpath through the channel;
(c) preselecting pyrolysis conditions for pyrolysis of the feed in the internal channel, wherein the pyrolysis conditions include a residence time in the channel ($t_R$) ≤1 sec., a feed conversion (X) ≥50%, an average total pressure in the channel (P) ≥1 bar, an average bulk gas temperature in the channel ($T_{av}$) ≤1500° C. at the start of the pyrolysis, a peak gas temperature ($T_P$) located in the channel, $T_P > T_{av}$, a pyrolysis step time $t_P$ in the range of from 0.001 sec. to 50 sec., and a change in average bulk gas temperature during the pyrolysis ($\Delta T_{av}$) ≤100° C.;
(d) predetermining the OFA using the formula $$([OFA-1]/OFA) = (t_R * \rho_s * C_P * R * T_{av} * \Delta T_{av})^{-1} * (t_P * X * \Delta H * P),$$

wherein R is substantially equal to the feed's Gas Constant;
(e) establishing a flow of the feed through the first opening, through the first aperture, and into the channel toward the second aperture at a flow rate ≥0.01 kg/s;
(f) carrying out the pyrolysis of the feed flow's $C_{2+}$ hydrocarbon in the channel under the preselected pyrolysis conditions during a pyrolysis time interval $t_P$, which cools the first channeled thermal mass and produces a flow of a pyrolysis product comprising molecular hydrogen, acetylene, $C_{2+}$ olefin, and coke; and
(g) during $t_P$, conducting the flow of at least a portion of the pyrolysis product into the second region of the internal volume via the second aperture, and away from the reactor via the second opening.

12. The process of claim 11, wherein X is ≥60 wt. %, $t_P$ is ≥2 seconds, and the average total pressure ≥5 psig, and the pyrolysis conditions further include a hydrocarbon partial pressure of ≥7 psia (48 kPa).

13. The process of claim 11, wherein $T_{av}$ and $T_P$ each decrease by no more than 75° C. during $t_P$.

14. The process of claim 11, wherein (i) the $C_{2+}$ olefin includes one or more of ethylene, propylene, and butylene, (ii) the pyrolysis product further comprises coke and one or more of acetylene, benzene, methane, and at least a portion of any unconverted feed, and (iii) at least a portion of the coke remains in the internal channel as a deposit.

15. The process of claim 11, wherein the feed comprises one or more of ethane, propane, butanes, saturated and unsaturated $C_6$ hydrocarbon, including those derived from one or more of Fischer-Tropsch synthesis products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$-residue admixture, naphtha-residue admixture, cracked feed, coker distillate streams, and hydrocarbon streams derived from plant or animal matter.

16. The process of claim 11, wherein the feed comprises ≥90 wt. % of hydrocarbon that is primarily in the liquid phase at a temperature of 25° C. and a pressure of 1 bar.

17. The process of claim 11, wherein at the start of $t_P$, $T_{av}$ is in the range of from 925° C. to 1075° C.

18. The process of claim 11, wherein the internal channel includes a plurality of substantially parallel passages having a having a passage density in the range of from 77000/m$^2$ to 1.3×10$^6$/m$^2$.

19. The process of claim 11, wherein $t_R$ is in a range of from 0.01 to 0.4 second, and the elongated channeled thermal mass includes at least one monolithic honeycomb having a mass ≥1 kg.

20. The process of claim 11, wherein the pyrolysis exhibits a first bulk gas temperature profile in the channel at the start of $t_P$, a second bulk gas temperature profile in the channel at the end of $t_P$, and the first and second bulk gas temperature profiles are substantially congruent.

21. A hydrocarbon pyrolysis process, the process comprising:
  (a) providing a feed comprising ≥1 wt. % of $C_{2+}$ hydrocarbon, wherein the feed has a pyrolysis heat of reaction ($\Delta H$) ≥1000 cal./mol and a Gas Constant (R);
  (b) providing an elongated flow-through reactor having (i) an internal volume which includes first and second regions, (ii) opposed first and second openings in fluidic communication with the internal volume, wherein the first and second openings are separated by a reactor length (L), and (iii) a channeled thermal mass located in the first region, wherein the first channeled thermal mass has a solid density ($\rho_s$) ≤12 g/cm$^3$, a heat capacity ($C_P$) ≤0.5 cal/g° C., and an open frontal area (OFA) ≤55%, and wherein the first channeled thermal mass includes:
    (A) a first aperture, the first aperture being proximate to the first opening and in fluidic communication with the first opening,
    (B) at least one internal channel in fluidic communication with the first aperture, and
    (C) a second aperture, the second aperture being in fluidic communication with the first aperture via a flowpath $L_1$ through the channel, $L_1$ being ≥0.1*$L_R$;
  (c) preselecting pyrolysis conditions for pyrolysis of the feed in the channel, wherein the pyrolysis conditions include a residence time in the channel ($t_R$) ≤1 sec., a feed conversion (X) ≥50%, an average total pressure in the channel (P) ≥1 bar, an average bulk gas temperature in the channel ($T_{av}$) ≤1100° C. at the start of the pyrolysis, a peak gas temperature ($T_P$) located in the channel, $T_P > T_{av}$, and a change in average bulk gas temperature during the pyrolysis ($\Delta T_{av}$) ≤75° C.;
  (d) predetermining a reference pyrolysis step time ($t_{ref}$) from $t_R$, $\rho_s$, $C_P$, R, $T_{av}$, $\Delta T_{av}$, OFA, X, $\Delta H$, R, and P; and
  (e) pyrolysing the feed in the channel under the preselected conditions during a pyrolysis time interval $t_P$ that does not exceed tee.

22. A hydrocarbon pyrolysis process, the process comprising:
(a) providing a feed comprising ≥1 wt. % of $C_{2+}$ hydrocarbon, wherein the feed has a pyrolysis heat of reaction (ΔH) ≥1000 cal./mol and a Gas Constant (R);
(b) providing an elongated flow-through reactor having (i) an internal volume which includes first and second regions, opposed first and second openings in fluidic communication with the internal volume, wherein the first and second openings are separated by a reactor length ($L_R$), and (ii) a first channeled thermal mass located in the first region, wherein the first channeled thermal mass has a solid density ($\rho_s$) ≤12 g/cm³, a heat capacity ($C_P$) ≤0.5 cal/g° C., and a predetermined open frontal area (OFA), and wherein the first channeled thermal mass includes:
(A) a first aperture, the first aperture being proximate to the first opening and in fluidic communication with the first opening,
(B) at least one internal channel in fluidic communication with the first aperture, and
(C) a second aperture, the second aperture being in fluidic communication with the first aperture via a flowpath $L_1$ through the channel, $L_1$ being ≥0.1*$L_R$;
(c) preselecting pyrolysis conditions for pyrolysis of the feed in the internal channel, wherein the pyrolysis conditions include a residence time in the channel ($t_R$) ≤1 sec., a feed conversion (X) ≥50%, an average total pressure in the channel (P) ≥1 bar, an average bulk gas temperature in the channel ($T_{av}$) ≤1100° C. at the start of the pyrolysis, a peak gas temperature ($T_P$) located in the channel, $T_P > T_{av}$, a pyrolysis step time $t_P$ that does not exceed a reference time ($t_{Ref}$) in the range of from 0.001 sec. to 50 sec., and a change in average bulk gas temperature during the pyrolysis ($\Delta T_{av}$) ≤75° C.;
(d) predetermining the OFA from $t_R$, $\rho_s$, $C_p$, R, $T_{av}$, $\Delta T_{av}$, $t_{Ref}$, X, ΔH, R, and P;
(e) establishing a flow of the feed through the first opening, through the first aperture, and into the channel toward the second aperture at a flow rate ≥0.01 kg/s;
(f) carrying out the pyrolysis of the feed flow's $C_{2+}$ hydrocarbon in the channel under the preselected pyrolysis conditions during a pyrolysis time interval $t_P$, which cools the first channeled thermal mass and produces a flow of a pyrolysis product comprising molecular hydrogen, acetylene, $C_{2+}$ olefin, and coke; and
(g) during $t_P$, conducting the flow of at least a portion of the pyrolysis product into the second region of the internal volume via the second aperture, and away from the reactor via the second opening.

23. The process of claim 22, wherein $t_{Ref}$ and OFA are predetermined by the equation $([OFA-1]/OFA*t_{Ref}) = (t_R*\rho_s*C_p*R*T_{av}*\Delta T_{av})^{-1}*(t_{Ref}*X*\Delta H*P)$.

* * * * *